(12) United States Patent
Kohara et al.

(10) Patent No.: US 9,222,890 B2
(45) Date of Patent: Dec. 29, 2015

(54) PLASMA SPECTROMETER

(75) Inventors: Yoshinobu Kohara, Tokyo (JP); Yuzuru Takamura, Nomi (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 162 days.

(21) Appl. No.: 14/000,610

(22) PCT Filed: Jan. 13, 2012

(86) PCT No.: PCT/JP2012/050552
§ 371 (c)(1),
(2), (4) Date: Aug. 21, 2013

(87) PCT Pub. No.: WO2012/120919
PCT Pub. Date: Sep. 13, 2012

(65) Prior Publication Data
US 2013/0321803 A1    Dec. 5, 2013

(30) Foreign Application Priority Data
Mar. 7, 2011    (JP) ................................. 2011-049041

(51) Int. Cl.
*G01J 3/30*    (2006.01)
*G01N 21/67*    (2006.01)
*G01N 21/69*    (2006.01)
*G01J 3/02*    (2006.01)

(52) U.S. Cl.
CPC ................ *G01N 21/67* (2013.01); *G01N 21/69* (2013.01); *G01J 3/02* (2013.01); *G01N 2201/08* (2013.01)

(58) Field of Classification Search
CPC .................................. G01N 21/67; G01J 3/02
USPC .................................................... 356/313, 316
See application file for complete search history.

(56) References Cited

U.S. PATENT DOCUMENTS

2007/0164003 A1    7/2007    Takamura et al.

FOREIGN PATENT DOCUMENTS

| JP | 4-52551 | 2/1992 |
|---|---|---|
| JP | 3932368 | 3/2007 |
| JP | 2010-197358 | 9/2010 |
| JP | 2011-180045 | 9/2011 |
| WO | WO 00/32017 | 6/2000 |

*Primary Examiner* — Gregory J Toatley
*Assistant Examiner* — Hina F Ayub
(74) *Attorney, Agent, or Firm* — Baker Botts L.L.P.

(57) ABSTRACT

To improve detection sensitivity, detection accuracy, and reproducibility when electric discharge is caused in a sample solution to perform analysis with light emission in the plasma,
a flow channel 101 provided with a narrow part is filled with a conductive sample solution, plasma is generated in bubbles formed by applying an electric field to the flow channel, and a region other than the narrow part in the flow channel is set as a measurement object region to measure light emission.

9 Claims, 21 Drawing Sheets

837μsec

AIR-LIQUID INTERFACE

1087μsec

LIGHT EMISSION

AIR-LIQUID INTERFACE a)

FLOW CHANNEL b)

0.8msec 0.1 N NITRIC ACID SOLUTION 1.8msec
CONTAINING 100 PPM OF LEAD 0.8msec 0.1 N NITRIC ACID SOLUTION 1.8msec 0.8msec DIFFERENCE IMAGE 1.8msec a)

FLOW CHANNEL   REGION φ0.34mm b)

○ : NET EMISSION INTENSITY OF LEAD (S)
● : BACKGROUND LIGHT INTENSITY (B)
× : S÷B(S/B)

c)

○ : NET EMISSION INTENSITY OF LEAD (S)
● : BACKGROUND LIGHT INTENSITY (B)
× : S÷B(S/B)

400 μm

BEFORE VOLTAGE APPLICATION

FLOW CHANNEL       400μm

AFTER VOLTAGE APPLICATION 100μsec

LIGHT EMISSION
AIR-LIQUID INTERFACE (NEGATIVE POLE SIDE)
AIR-LIQUID INTERFACE (POSITIVE POLE SIDE)
FLOW CHANNEL       400μm

NARROW PART

PLASMA SPECTROMETER

TECHNICAL FIELD

The present invention relates to a plasma spectrometer which analyzes a liquid sample by using plasma emission.

BACKGROUND ART

As a background art of the invention, there is Japanese Patent No. 3932368 (PTL 1). PTL 1 describes a plasma generation method in which a flow channel made of an insulating material is provided with a narrow part having a much smaller cross-sectional area than that of the flow channel, the flow channel and the narrow part are filled with a conductive liquid, and then an electric field is applied to the narrow part to pass the electric field through the narrow part, thereby generating plasma, and an element analysis method. A plasma generator in which a flow channel made of an insulating material is installed with a narrow part having a much smaller cross-sectional area than that of the flow channel and means for applying an electric field to the narrow part to pass the electric field through the narrow part is installed, and an emission spectrometer having the plasma generator are also described.

CITATION LIST

Patent Literature

PTL 1: Japanese Patent No. 3932368

SUMMARY OF INVENTION

Technical Problem

In PTL 1, there is a description that bubbles are formed in the narrow part to generate plasma in the formed bubbles. In addition, there is a description that when the generated plasma is formed larger to be equal to or greater than the volume of the narrow part of the flow channel, the shape and the brightness of the plasma remarkably change, and thus a variation in emission intensity is large. However, there is no description that when bubbles and plasma are formed much larger than the size of the narrow part, a phenomenon which has not been known occurs, and thus detection sensitivity, detection accuracy, and reproducibility are improved.

In PTL 1, there is a description that accurate measurement can be conducted by adjusting electrical conductivity of a sample to electrical conductivity convenient for the plasma generation and the measurement. However, there are no descriptions of the measurement of a temporal change in the current at the time of voltage application, and an improvement in detection sensitivity, detection accuracy, and reproducibility by using information of the temporal change in the current.

The invention is to improve detection sensitivity, detection accuracy, and reproducibility in a method in which electric discharge is caused in a sample solution and light emission in the plasma is used to perform analysis.

Solution to Problem

The invention includes a plurality of means for solving the problems, and an example thereof is a spectrometer in which a flow channel provided with a narrow part is filled with a conductive liquid, bubbles are formed by applying an electric field to the flow channel, and plasma is generated in the bubbles, and a region other than the narrow part in the flow channel is set as a measurement object region.

Another example is a spectrometer in which a flow channel is filled with a conductive liquid, bubbles are formed by applying an electric field to the flow channel, and plasma is generated in the bubbles, and one or more specific times of light emission after second light emission are measured among a plurality of times of light emission which are caused with a single voltage application.

A further example is a spectrometer in which a flow channel is filled with a conductive liquid, bubbles are formed by applying an electric field to the flow channel, and plasma is generated in the bubbles, and a timing of light emission measurement is controlled using a temporal change in the current at the time of electric field application.

Advantageous Effects of Invention

According to the invention, detection sensitivity, detection accuracy, and reproducibility can be improved in a method in which electric discharge is caused in a sample solution and light emission in the plasma is used to perform analysis.

Objects, configurations, and effects other than those described above will become apparent from the descriptions of the following embodiments.

DESCRIPTION OF EMBODIMENTS

Figure 1:
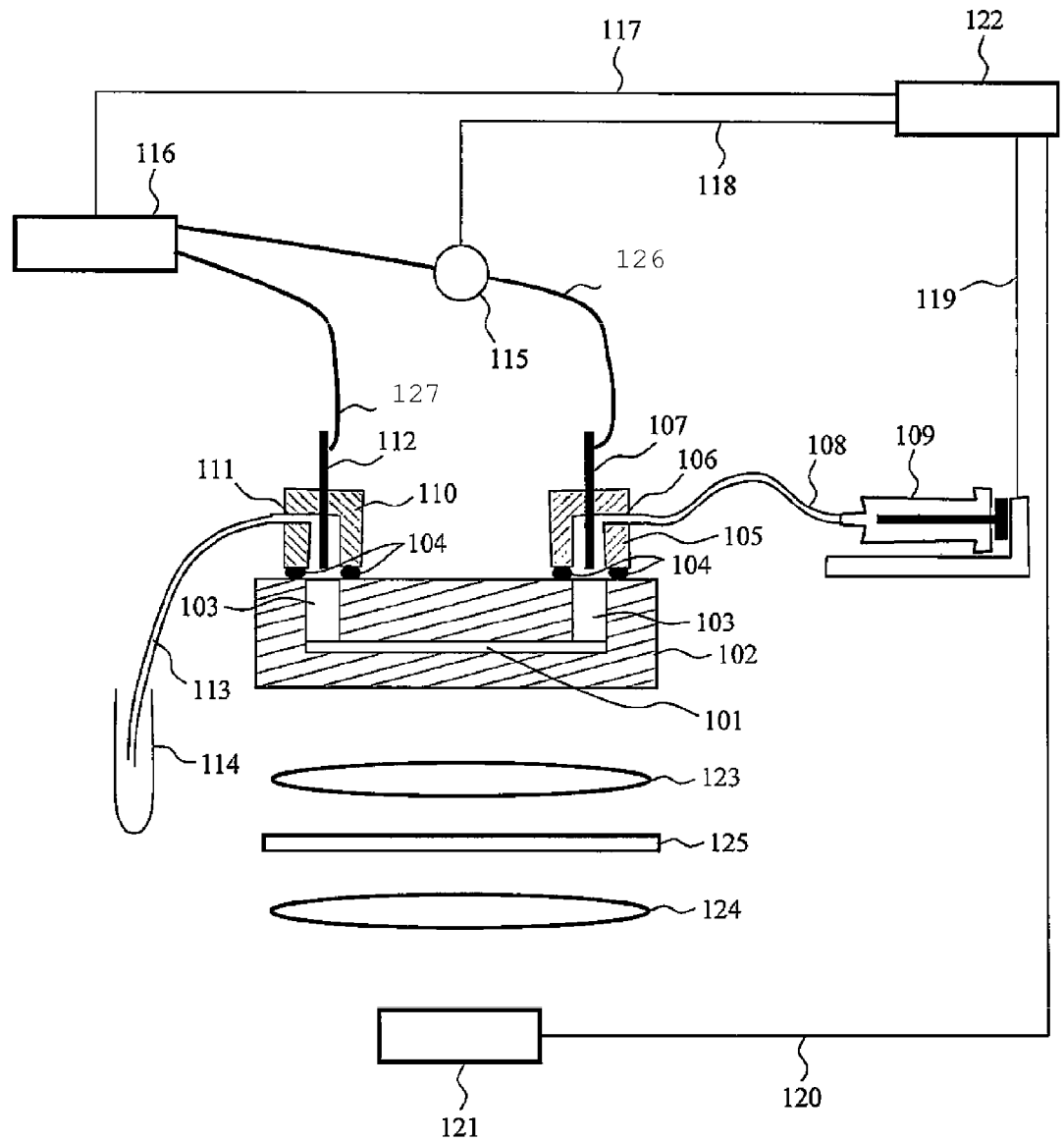
FIG. 1 is a diagram showing an example of a configuration of a plasma emission spectrometer.

In the invention, bubbles are formed much larger than the size of a narrow part and plasma is formed much larger than the narrow part. As a result, a phenomenon which has not been known occurs and a region other than the narrow part of a flow channel becomes a measurement object. Thus, it is possible to improve detection sensitivity. In addition, when bubbles are formed much larger than the size of the narrow part and plasma is formed much larger than the narrow part, it is possible to perform the measurement out of the narrow part.

Since the sizes of the bubbles and the plasma vary with the shape of the flow channel, the electrode arrangement, the composition of a sample solution and the like, other than the magnitude of an application voltage and a voltage application time, it is difficult to unconditionally specify generation conditions of the bubbles and the plasma. However, the application voltage is preferably 500 V or greater, more preferably 1 kV or greater, even more preferably 1.5 kV or greater, and most preferably 2.5 kV or greater. The voltage application time is preferably 0.1 msec or longer, more preferably 0.2 msec or longer, even more preferably 0.5 msec or longer, and most preferably 0.8 msec or longer.

The sample solution is required to have an electrical conduction property. An acid such as a nitric acid which is commonly used in element analysis is appropriate. Various acids such as a hydrochloric acid and a sulfuric acid can also be used, and solutions containing salts having an electrical conduction property can also be used.

Since a region which is appropriate as a measurement object is in a range in which bubbles and plasma are present, and depends on the sizes of bubbles and plasma, it is difficult to unconditionally specify the region. However, the region can be thought as follows based on a length b of the narrow part in a voltage application direction. A distance between a center of the narrow part and a center of the region which becomes a measurement object is preferably 5 times or greater, more preferably 3 times or greater, even more preferably 2 times or greater, and most preferably 1 time or greater the length b. Since light emission is caused in a range in which bubbles and plasma are present, an appropriate range of the measurement object region is up to the most distant flow channel from the center of the narrow part.

Since conditions of causing a plurality of times of light emission with a single voltage application vary with the shape of the flow channel, the electrode arrangement, and the composition of a sample solution, other than an application voltage and a voltage application time, it is difficult to unconditionally specify the causing conditions. However, the conditions are almost the same as those in the case in which bubbles and plasma are formed sufficiently larger than the size of the narrow part. A voltage to be applied to the flow channel with the narrow part interposed therein is preferably 500 V or greater, more preferably 1 kV or greater, even more preferably about 1.5 kV or greater, and most preferably 2.5 kV or greater. The voltage application time is preferably 0.5 msec or longer, and more preferably 0.8 msec or longer.

As described below, the light emission is closely related to the rise and fall of the current, but a current peak immediately after voltage application corresponds to from an increase of the current by voltage application to an increase of electric resistance and a reduction of a current value due to the formation of bubbles by Joule heat, and the light emission is not almost observed. Accordingly, excluding the peak of the current value immediately after voltage application, from the next current peak, respective current peaks are accompanied with light emission, and a plurality of times of light emission occur on the condition that a plurality of current peaks are observed.

There are roughly two methods in the case in which a light emission measurement timing is controlled using a temporal change in the current at the time of electric field application. One method is a measurement method in which an exposure timing is controlled to integrate and measure all of light emission in an appropriate time zone. For example, the method can be applied to a case of detecting light emission by using a CCD camera as a detection element. In this case, for example, when a temporal change in the current is simultaneously measured and the current value satisfies a pre-set condition, an exposure signal is transmitted to the detector and the light emission is measured. In addition, in another mode, a temporal change in the current is measured under the same conditions, an exposure timing is determined in advance from the recorded temporal change in the current, and by using the exposure timing, light emission can be measured.

The other method is a method in which all of temporal changes of light emission are recorded in a storing device such as a memory, and after the end of voltage application, a light emission amount in an appropriate time zone is read or integrated from the recorded temporal changes of light emission. For example, the method can be applied to a case of detecting light emission by using a photomultiplier as a detection element. In this case, for example, a temporal change in the current is simultaneously recorded in a storing device such as a memory, and after the end of voltage application, the light emission data is processed using the recorded temporal change in the current. In addition, in another mode, a temporal change in the current is measured in advance under the same conditions, and a time zone in which the light emission data is to be read or integrated can be determined from the recorded temporal change in the current.

In addition, a temporal change in the current at the time of electric field application is measured with respect to an analysis object substance-containing sample solution, and then a reference solution is adjusted so that a temporal change in the current of the reference solution at the time of electric field application matches the temporal change in the current of the sample solution, a voltage is applied to the reference solution after adjustment to measure light emission, and the amount of the analysis object substance in the sample solution can be estimated with reference to the measured emission intensity.

When knowing a main composition of the sample solution, it is preferable to use a solution containing a type of element constituting the main composition as the reference solution. For example, when knowing the acid type, it is preferable to use the same type of acid. Since a nitric acid is frequently used in element analysis, it is appropriate to use a nitric acid in many cases. It is also appropriate to use other acids such as a hydrochloric acid and a sulfuric acid. In addition, when the electrical conductivity of the sample solution is derived mainly from the salt which is dissolved, it is appropriate to use a solution containing the same type of salt, and examples of the salt include sodium chloride and potassium chloride. In addition, when the sample solution contains an organic solvent, it is also appropriate to use an adjustment solution containing an organic solvent. Examples of the organic solvent include ethanol and acetone.

The above adjustment means that, for example, when a nitric acid is used, a temporal change in the current at the time of voltage application is measured with respect to a solution in which the mixing ratio between a high-concentration nitric acid and water is gradually changed, and a solution having the closest temporal change in the current to the temporal change in the current at the time of voltage application to the sample solution is selected or a solution in which the mixing ratio is changed to achieve the temporal changes of current close to each other is prepared. The solution selected or prepared in this manner is used as a reference solution. When a reference solution other than a nitric acid is used, this type of solution having a high concentration may be adjusted by changing a water mixing ratio so that a temporal change in the current of the solution is close to the temporal change in the sample solution, and this solution may be set as a reference solution. Water is easily used in a combination of an element to be mixed, but the combination is not limited thereto. Three or more types of solutions may be combined.

Regarding the reference solution, it is also effective to adjust a solution containing an element which is a measurement object. By adjusting and using a reference solution containing an element which is a measurement object, it is possible to plot a more accurate calibration curve and improve detection sensitivity, detection accuracy, and reproducibility.

According to the invention, even when a sample solution contains an element which is an analysis object at such a low concentration that it has not been possible to analyze the element in the past, the element can be detected and accurately quantified. In addition, for example, a sample solution containing an element which is an analysis object at such a too low concentration that it has not been possible to detect the element in the past when not performing a concentration process before the analysis can be analyzed without the concentration process. In addition, for example, even an analysis object which is not appropriate to be subjected to the concentration process can also be analyzed. In addition, for example, a sample solution which is not appropriate to be diluted because when diluting the sample solution, it has not been possible to perform detection in the past due to a reduced concentration of an element which is an analysis object can be analyzed after dilution. In addition, for example, even with a sample solution which has been required to be analyzed more than once in the past because of its poor reproducibility in the detection, it is possible to obtain results having high reliability through a much smaller number of analysis including one time.

Hereinafter, embodiments of the invention will be described with reference to the drawings.

Embodiment 1

In this embodiment, an example of a configuration of a plasma emission spectrometer will be described. Also, a luminescence phenomenon occurring by electric discharge of a sample solution, and novel knowledge leading to the invention will be described.

FIG. 1 is a schematic diagram showing an example of a configuration of a plasma spectrometer of this embodiment.

A flow channel 101 is formed in quartz glass 102. A solution can be allowed to flow to the flow channel 101 through through holes 103 on the upstream side and the downstream side of the flow channel 101. Connectors 105 and 110 press O-rings 104 against the quartz glass 102 to prevent liquid leakage when a solution flows to the flow channel 101 from the outside. The connectors 105 and 110 have electrodes 107 and 112 attached thereto, respectively, whereby it is possible to apply a voltage to the solution in the flow channel 101. In this embodiment, platinum wires having a diameter of 0.5 mm are used as the electrodes 107 and 112. The connectors 105 and 110 are provided with pipe connecting ports 106 and 111, respectively.

A pipe 108 is connected to the pipe connecting port 106 of the connector 105, and a syringe pump 109 is connected to the pipe 108. The solution in the syringe pump 109 can be transmitted to the flow channel 101 by controlling the syringe pump 109. The syringe pump 109 is connected to a computer 122 via a signal wire 119, and the operation is controlled by the computer 122. A pipe 113 is connected to the pipe connecting port 111 of the other connector 110, and a waste liquid container 114 is installed ahead of the pipe 113.

The electrodes 107 and 112 are connected to a power supply 116 via high-voltage electric wires 126 and 127, respectively. In this embodiment, a DC pulsed power supply is used as the power supply 116. An ammeter 115 for current measurement is connected in series in the middle of the high-voltage electric wire 126.

The computer 122 is connected to the power supply 116 via a signal wire 117. The computer 122 can set an output voltage of the power supply 116 and perform ON/OFF timing control using a trigger on the basis of input information. The computer 122 is connected to the ammeter 115 via a signal wire 118 to load measurement data of the ammeter 115 thereonto, and can use the measurement data in the control of the power supply 116 by processing the measurement data.

A camera 121 is connected to the computer 122 via a signal wire 120. The computer 122 reflects input camera setting information in the setting of the camera 121, and an image photographed by the camera 121 is recorded and processed in the computer 122. In addition, the computer 122 outputs a signal for exposure control for the camera 121, and the camera 121 receives the signal for exposure control and is operated.

The light emission occurring in the flow channel 101 is photographed by the camera 121 via lenses 123 and 124. When information of emission wavelength is acquired, an optical filter 125 is installed to be able to acquire an image responding to the transmission characteristics of the optical filter 125. The lens 123 is installed on the opposite side of the connectors 105 and 110 with respect to the flow channel 101, and it is important to perform photographing so that the entire flow channel is not hidden behind the connectors 105 and 110. Since dimensions of bubbles and plasma related to the light emission are large, the surroundings of the connectors are hidden behind the connectors when the photographing is performed on the connector side. Thus, the photographing cannot be performed.

Data related to the light emission which has been photographed by the camera 121 and recorded in the memory of the computer 122, and data related to the temporal change in the current which has been measured by the ammeter 115 and recorded in the memory of the computer 122 can also be combined and processed by the computer 122. As described above, the computer 122 simultaneously performs a function as a controller and a function as an arithmetic processor.

Figure 2:
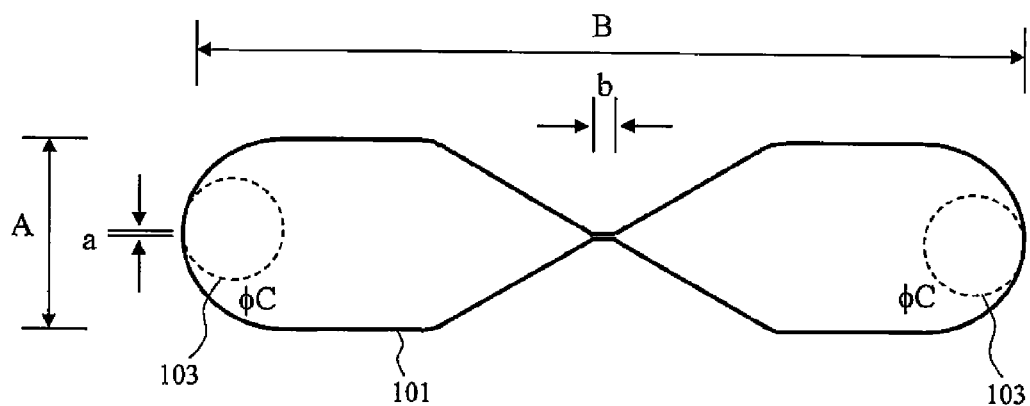
FIG. 2 is a diagram showing an example of a flow channel.

FIG. 2 is a diagram illustrating an example of the flow channel 101 used in this embodiment. The flow channel 101 having a width A and a length B is a flow channel having a uniform depth which is provided with a narrow part having a width a and a length b at the center thereof. The width a of the narrow part is narrower than the width A of the flow channel, and is preferably 1/3 or less, and more preferably 1/10 or less of the width A of the flow channel. The length b of the narrow part is shorter than the length B, and is preferably 1/5 or less, and more preferably 1/10 or less of the length B. The length B of the flow channel is preferably 1 mm to 30 cm. The depth of the flow channel is preferably almost the same as the width of the narrow part, or almost the same or less than the length of the narrow part. In this embodiment, the width A of the flow channel is 3 mm, the length B of the flow channel is 13 mm, the width a of the narrow part is 0.10 mm, the length b of the narrow part is 0.40 mm, and the depth of the flow channel is 0.08 mm. The positions of the through holes 103 on the right and left sides of the flow channel 101 are shown by the broken line. The diameter of the through hole 103 is preferably almost the same as the internal hole diameter of the connector in order to prevent a reduction in reproducibility due to bubbles and the like adhering to the difference in level of the connecting part with the connector.

Regarding the plasma emission spectrometer shown in FIGS. 1 and 2, procedures for photographing light emission including: supplying a 0.1 N nitric acid solution containing 100 ppm of lead as a sample solution to the flow channel; and applying a voltage will be shown as follows. Using the lead-containing solution as a sample solution is just an example for description. A solution containing another element can also be analyzed with the same procedures, and the same phenomenon and the same effect can be observed.

First, water is allowed to flow to the empty flow channel 101, and then a 0.1 N nitric acid is allowed to flow thereto to perform washing. First, water is put into the syringe of the syringe pump 109, and the syringe pump 109 is operated with an instruction from the computer 122 to allow the water to flow to and wash the flow channel 101 via the pipe 108, the pipe connecting port 106, the inside of the connector 105, and the through hole 103, and the water after washing is recovered to the waste liquid container 114 via the through hole 103 on the downstream side, the inside of the connector 110, the pipe connecting port 111, and the pipe 113. Next, a 0.1 N nitric acid is allowed to flow with the same procedures to wash the flow channel 101.

Next, a 0.1 N nitric acid solution containing 100 ppm of lead which is a sample solution is allowed to flow to the flow channel 101 with the same procedures, and light emission is caused by applying a voltage. An appropriate application voltage is preferably 500 V or greater, more preferably 1 kV or greater, even more preferably 1.5 kV or greater, and most preferably 2.5 kV or greater. Here, the application voltage is 2.5 kV, and the voltage application pulse width is 0.8 msec or 1.8 msec. In this embodiment, the polarities of the power supply 116 are set so that a positive high voltage is applied to the side of the high-voltage electric wire 127 and the side of the high-voltage electric wire 126 becomes ground. That is, the polarities of the electrodes are set so that the electrode 107 on the upstream side of the transmitted sample solution is a negative pole and the electrode 112 on the downstream side of the transmitted sample solution is a positive pole. The relationship between the electrode polarity and the direction of the flow of the sample solution is not limited to this combination. The reverse combination is also possible.

The computer 122 generates a voltage application start signal. The power supply 116 receives the signal from the computer 122 and applies a voltage to the flow channel 101 in response to the signal. The camera 121 controls the exposure by inputting the same signal as the voltage application signal to the camera 121 from the computer 122. The ammeter 115 measures the current by outputting, from the computer 122, a signal synchronized with the signal for starting the application of a voltage to the power supply 116 and by inputting the signal to the ammeter 115.

Figure 3:
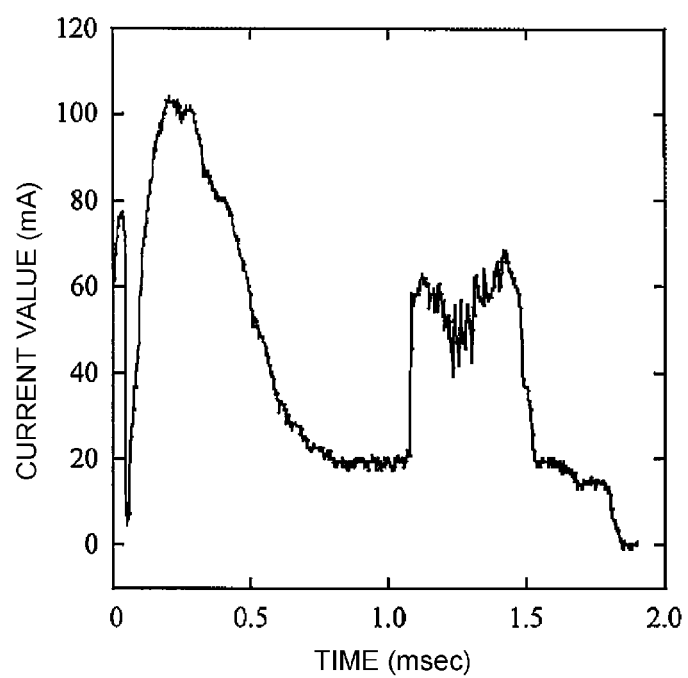
FIG. 3 is a diagram showing a temporal change in a current.

FIG. 3 is a diagram showing a temporal change in the current which is measured by the ammeter 115 in this embodiment. The vertical axis represents a current, and the horizontal axis represents a time. A voltage application start time is set as a zero time. The voltage application pulse width is 1.8 msec. Three peaks, that is, a current peak in the vicinity of 0.05 msec which has a maximum value of about 80 mA immediately after voltage application, a current peak which has a smooth peak for up to 0.8 msec after voltage application, and a current peak which rises sharply after 0.8 msec after voltage application are observed.

As will be described later, the light emission is closely related to the rise and fall of the current, but a current peak immediately after voltage application corresponds to from an increase of the current by voltage application to an increase of electric resistance and a reduction of a current value due to the formation of bubbles by Joule heat, and at this time, the light emission is not almost observed. Accordingly, excluding the peak of the current value immediately after voltage application, the current peaks are counted in order, and the number of times of light emission is counted in that order. In this embodiment and Embodiments 2 and 3, specifically, the light emission corresponding to a peak up to 0.8 msec after voltage application is described as first light emission, and the light emission corresponding to a peak from after 0.8 msec to after 1.8 msec after voltage application is described as second light emission.

FIGS. 4A to 4J are examples of images which are photographed by a high-speed camera and show bubbles which are formed at the time of voltage application and a light emission state in this embodiment. The photographed images are shown in order of time from when the voltage application is started. The time shown in the upper left part of each drawing represents an elapsed time with a voltage application start time as a base point. Using a high-speed camera as the camera 121 shown in FIG. 1, the photographing is performed simultaneously with the measurement of the temporal change in the current shown in FIG. 3. In the photographing, the flow channel is illuminated to make the flow channel more visible, and the optical filter 125 is not used.

Figure 4A:
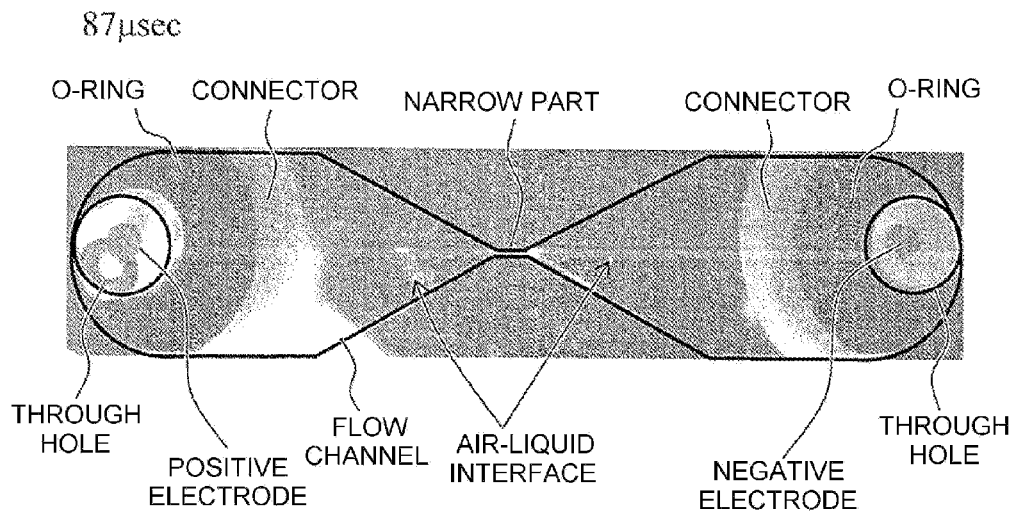
FIG. 4A is an image showing bubbles and a light emission state.

FIG. 4A is an image with a description attached thereto, which is photographed after 87 microseconds after voltage application. First, a flow channel and the surroundings thereof common to all of FIGS. 4A to 4J will be described. There is a flow channel having a narrow part at the center thereof, and there are through holes on both sides of the flow channel. Platinum wires as electrodes having a diameter of 0.5 mm are disposed in the through hole. The electrode on the right side is a negative electrode, and the electrode on the left side is a positive electrode. A sample solution flows from the right side to the left side in the drawing. Since the flow channel is photographed on the opposite side of the connector, the inside of the flow channel can be observed without disturbance of the O-rings and the connectors in the drawing.

The flow channel before voltage application is filled with a sample solution, and needless to say, no air-liquid interface is present. However, in FIG. 4A after voltage application, air-liquid interfaces can be observed at positions which are almost bilaterally symmetrical from the narrow part of the flow channel. This indicates that bubbles formed in the narrow part spread almost evenly to the right and left. The narrow part side of the air-liquid interface corresponds to the bubbles, and both electrode sides of the air-liquid interface corresponds to the sample solution.

Figure 4B:
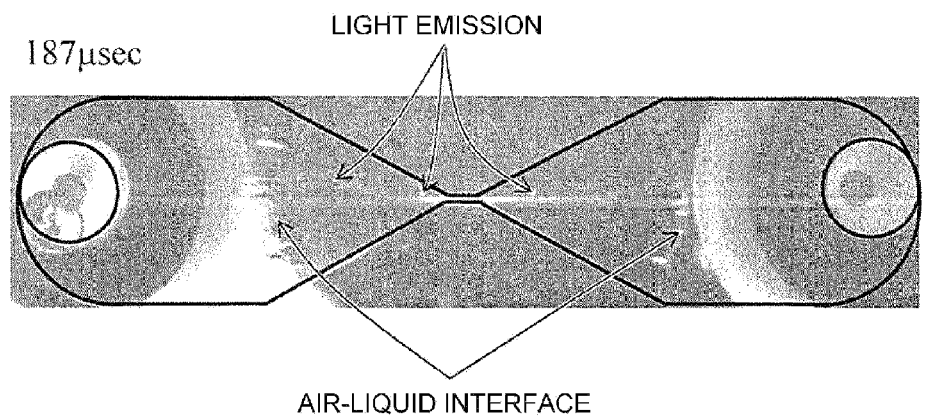
FIG. 4B is an image showing bubbles and a light emission state.

FIG. 4B is an image with a description attached thereto, which is photographed after 187 microseconds after voltage application. The bubbles are formed much larger than in the narrow part of the flow channel, and thus air-liquid interfaces can be observed at positions greatly separated from the narrow part and adjacent to the connectors. In addition, linear light emission is shown, which greatly expand to the right and left through the narrow part. In FIG. 4B, each light emission is linearly shown so as to almost horizontally expand toward the right side from the narrow part and to expand to the slightly upper left toward the left side. The light emission which is linearly shown is at a slightly different position every voltage application pulse, but in most cases, the light emission is adjacent to the line connecting the narrow part and both the electrodes. The light emission is caused by plasma. From FIG. 4B, it is found that under these conditions, the bubbles, the light emission, and the plasma are present in a region much larger than the narrow part.

Figure 4C:
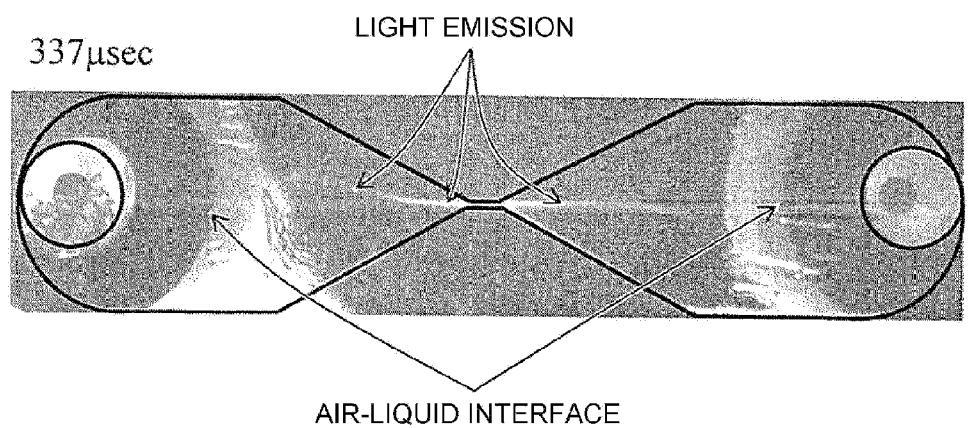
FIG. 4C is an image showing bubbles and a light emission state.

FIG. 4C is an image with a description attached thereto, which is photographed after 337 microseconds after voltage application. Under the conditions of this embodiment, the largest bubbles are formed at this timing, and the white lines representing the light emission in the drawing are the most densely photographed. The air-liquid interface is separated by a distance of about 4 mm when measured from the center of the narrow part, and the distance is about 10 times the length (0.4 mm) of the narrow part. The first light emission has the highest emission intensity at approximately this timing, and the light emission is not obviously limited to the narrow part, but protrudes greatly from the narrow part. For example, in spite of depending on the sensitivity of the camera also, the light emission separated up to a distance of about 3 mm from the center of the narrow part can be observed, and the light emission separated by a distance up to about 8 times the length (0.4 mm) of the narrow part can be observed.

As shown in FIGS. 4A to 4C, under the conditions of this embodiment, the bubbles are formed larger centrosymmetrically with the lapse of time, and protrude greatly further from the narrow part. It is found that with the swelling of the bubbles, a pressure higher than 1 atmosphere is applied to the inside of the bubbles.

Figure 4D:
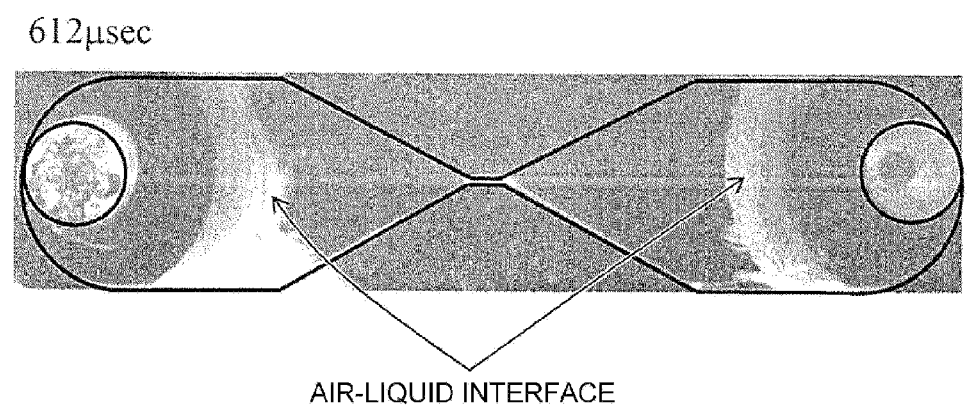
FIG. 4D is an image showing bubbles and a light emission state.
Figure 4E:
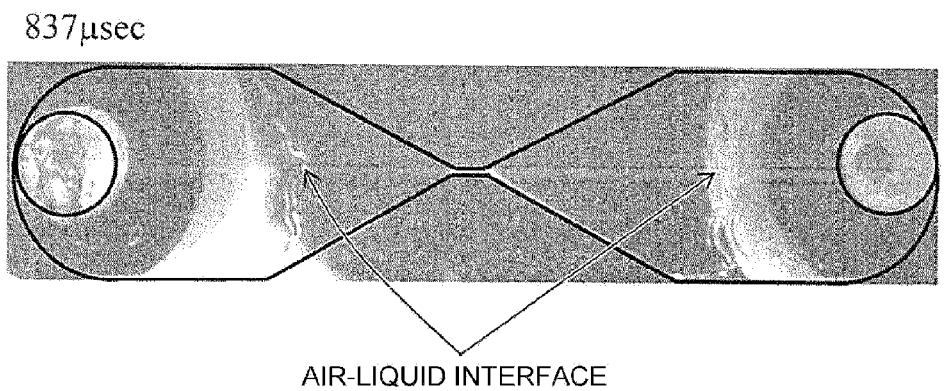
FIG. 4E is an image showing bubbles and a light emission state.

FIG. 4D is an image after 612 microseconds after voltage application, and FIG. 4E is an image after 837 microseconds after voltage application. A description is attached to each of FIGS. 4D and 4E. In FIGS. 4D and 4E, it is found that the bubbles are shrunk and the emission intensity is reduced. Particularly, it is not possible to confirm a clear line of light emission at the timing of FIG. 4E. The strong light which is shown in the narrow part is due to the scattering of the illumination light by the glass of the narrow part, and the light emission is not a main cause thereof. As shown in FIG. 3, this timing is equivalent to a region in which the current value corresponding to the first light emission is almost completely reduced.

Figure 4F:
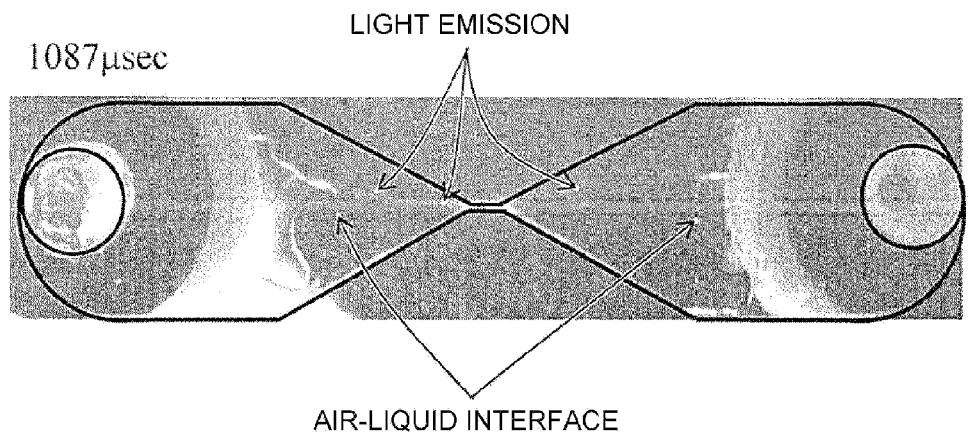
FIG. 4F is an image showing bubbles and a light emission state.

FIG. 4F is an image with a description attached thereto, which is photographed after 1087 microseconds after voltage application. In FIG. 4F, a timing at which the second light emission is started is taken. A convex form in which the air-liquid interface on the positive pole side which is disposed on the left side when viewed from the narrow part is toward the right is formed, and electric discharge is caused between the tip end of the convex part and the air-liquid interface on the negative pole side which is disposed on the right side when viewed from the narrow part, thereby causing light emission. The position of the air-liquid interface is separated by a distance of about 2 mm from the center of the narrow part, and the distance is about 5 times the length (0.4 mm) of the narrow part.

As found in FIG. 3, the current is rapidly increased at the timing at which the second light emission is started. As a result of the repetitive photographing, the average distance between the air-liquid interfaces on both sides at the timing at which the second light emission is started is 4.5 mm. Paschen's law is established and a substance-specific relationship which is expressed by Paschen curve is formed between an electric discharge start voltage V and a product of a substance pressure p and an electric discharge distance d. When the distance between the air-liquid interfaces and the application voltage are applied to the Paschen curve of water vapor, the internal pressure of the bubbles is about 0.1 atmosphere, and it is found that the pressure is reduced.

Figure 4G:
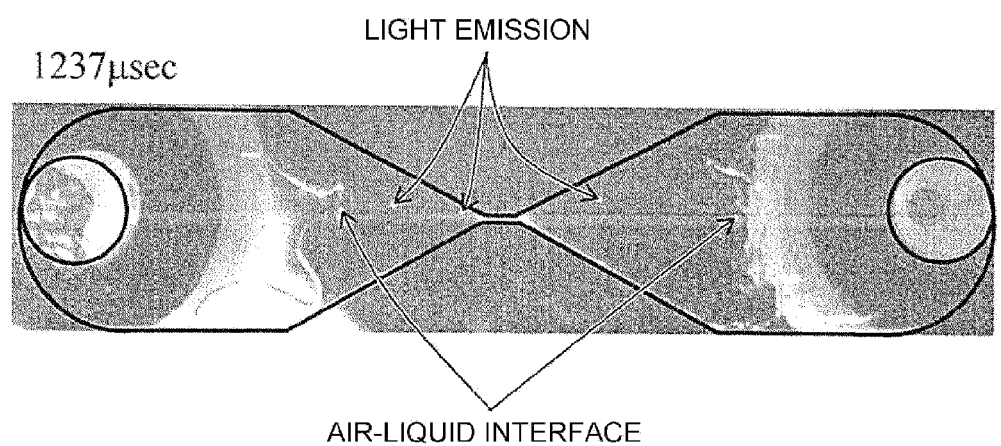
FIG. 4G is an image showing bubbles and a light emission state.
Figure 4H:
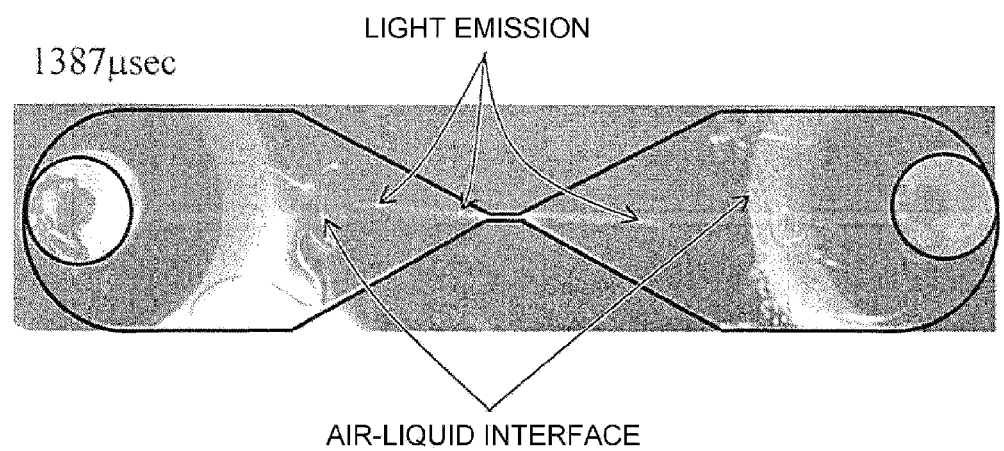
FIG. 4H is an image showing bubbles and a light emission state.

FIG. 4G is an image after 1237 microseconds after voltage application, and FIG. 4H is an image after 1387 microseconds after voltage application. A description is attached to each of FIGS. 4G and 4H. FIGS. 4G and 4H are imaged during the second light emission, and it is found that the tip end of the convex part of the air-liquid interface on the positive pole side which is disposed on the left side when viewed from the narrow part is gradually pushed and changed into an open form, and the position of the tip end does not greatly move. On the other hand, in the case of the air-liquid interface on the negative pole side which is disposed on the right side when viewed from the narrow part, the shape is greatly changed in the middle of the second light emission and it can be seen as if it is blown away. The air-liquid interfaces on both sides are separated from the narrow part and move in a direction in which the bubbles are formed larger.

Figure 4I:
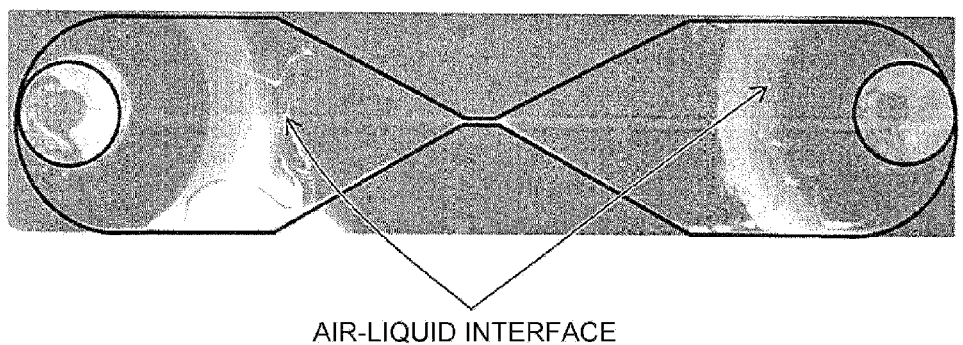
FIG. 4I is an image showing bubbles and a light emission state.

FIG. 4I is an image with a description attached thereto, which is photographed after 1512 microseconds after voltage application. In FIG. 4I, a timing at which the second light emission is stopped is taken. As found in FIG. 3, the current is rapidly reduced at the timing at which the second light emission is stopped. It is thought that the distance between the air-liquid interfaces is increased due to the electric discharge, a voltage necessary for the electric discharge is not sufficient with respect to the distance, the electric discharge is stopped, and the light emission is stopped.

Figure 4J:
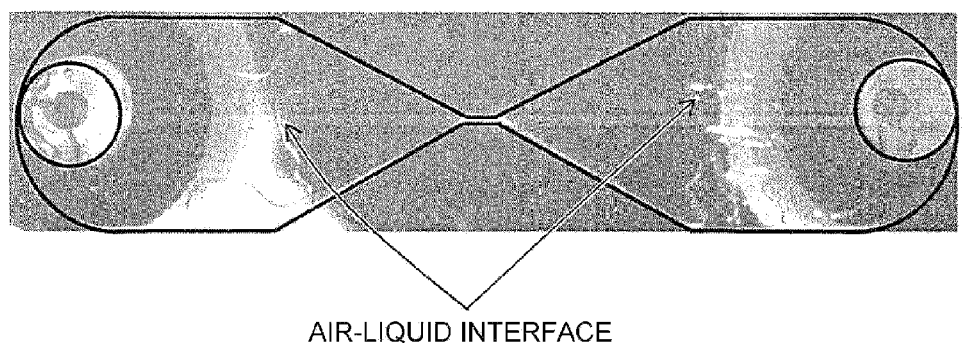
FIG. 4J is an image showing bubbles and a light emission state.

FIG. 4J is an image with a description attached thereto, which is photographed after 1812 microseconds after voltage application. FIG. 4J is an image immediately after the voltage application is stopped. The light emission is not observed as in FIG. 4I.

As described using FIGS. 3 and 4A to 4J, it is found that the current value is closely correlated to the behaviors of the bubbles and the light emission. It is also found that under the conditions of this embodiment, the bubbles are formed much larger than the size of the narrow part and a plurality of times of light emission can be realized with a single voltage application.

Figure 5:
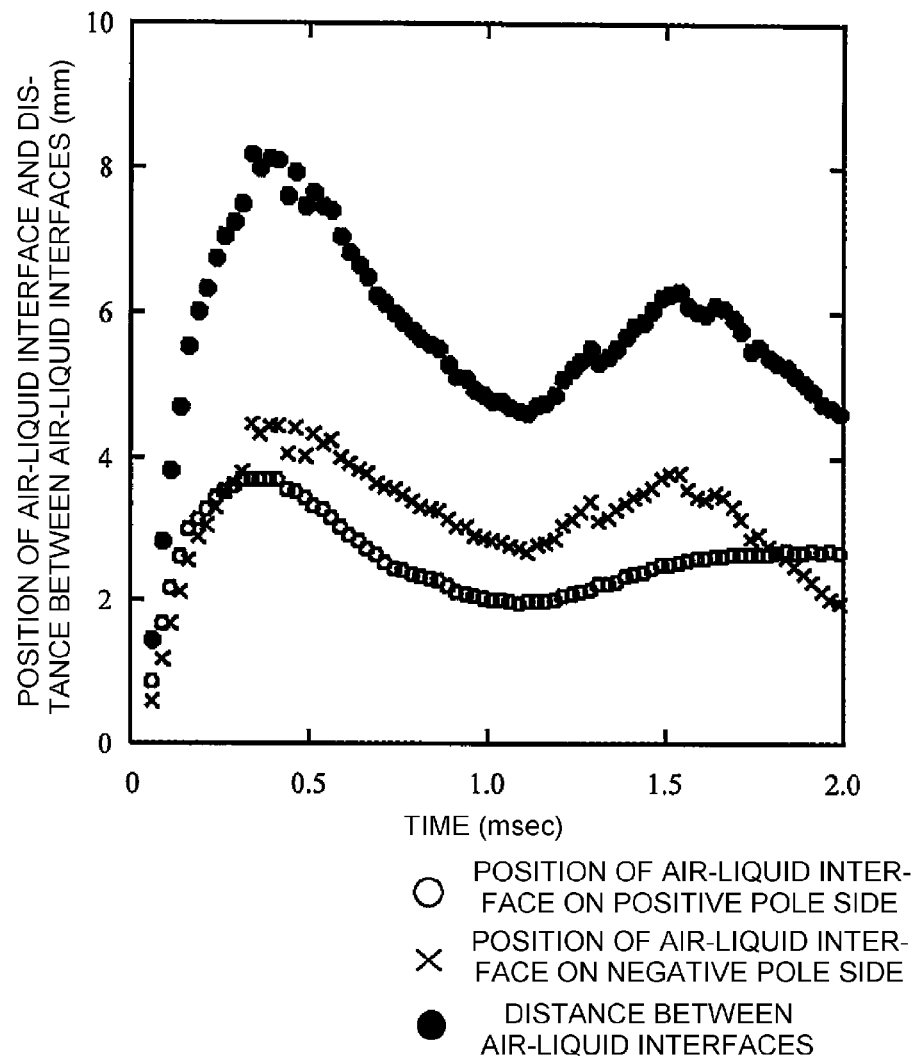
FIG. 5 is an explanatory diagram illustrating temporal changes of bubbles.

FIG. 5 is a diagram illustrating temporal changes of positions of the air-liquid interfaces and a distance between the air-liquid interfaces. This drawing is plotted using the same photograph data as FIGS. 4A to 4J. Regarding any of the air-liquid interfaces on the left side (positive pole side) and on the right side (negative pole side), the position of the air-liquid interface is an absolute value which is measured with the center of the narrow part as an origin, and the distance between the air-liquid interfaces is equivalent to the sum of the positions of the air-liquid interfaces on both sides.

It is found that the position of the air-liquid interface is separated at a maximum distance of about 4 mm or greater from the center of the narrow part, although there is a slight difference between the air-liquid interfaces on the positive pole side and on the negative pole side. In addition, it is found that the distance between the air-liquid interfaces is expanded up to about 8 mm. Any of these is equivalent to a region much larger than the size of the narrow part. When the length of the narrow part is set as a representative size of the narrow part, it is found that the distance from the center of the narrow part is increased up to about 10 times the size of the narrow part, and in terms of bubble size, the bubbles spread throughout a size which is about 20 times the size of the narrow part.

When being calculated from the relationship between the position of the air-liquid interface and the time, the speed at which the bubbles spread is high, e.g., about 100 km per hour.

In addition, at a time point when the second light emission is started, corresponding to FIG. 4F, the position of the air-liquid interface on the positive electrode side is about 2 mm, and it is found that the bubbles are then formed larger. At this time point, the bubbles spread over a region much larger than the narrow part. When the length (0.4 mm) of the narrow part is set as a representative size of the narrow part, it is found that the bubbles spread throughout a size about 5 times the size of the narrow part from the center of the narrow part.

Figure 6:
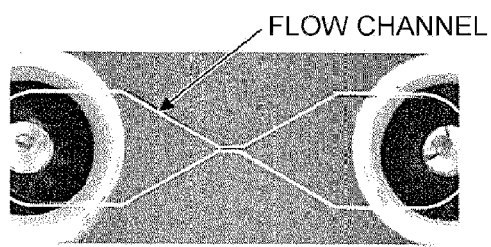
FIG. 6 shows examples of spatial distributions of light emission.
Figure 6:
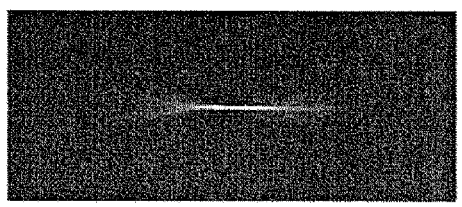
Figure 6:
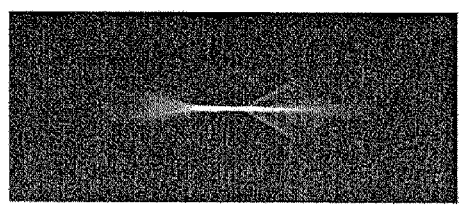
Figure 6:
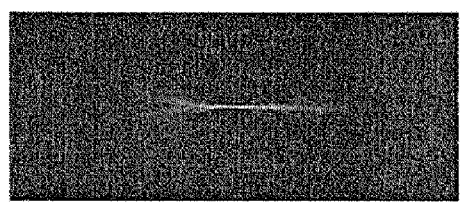
Figure 6:
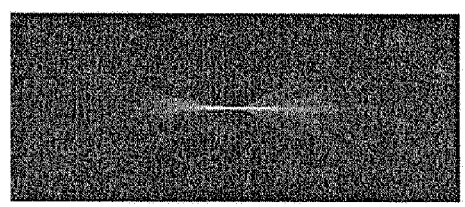
Figure 6:
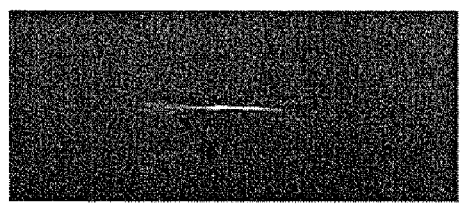
Figure 6:
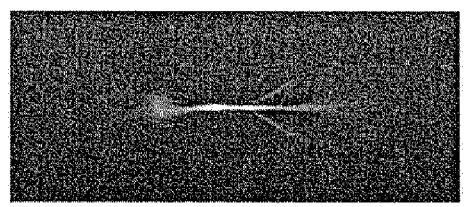

FIG. 6 illustrates examples of emission distributions observed in this embodiment. The photographing is performed by using a cooled CCD camera as the camera 121 shown in FIG. 1. As the optical filter 125, a band pass filter having a center wavelength of 405 nm and a half-value width of 10 nm is used. It is possible to observe atomic emission of lead through this optical filter since neutral atoms (PbI) of lead have an emission line at a wavelength of 405.78 nm.

FIG. 6(a) is an explanatory diagram showing the position of the flow channel and the like in the drawing, in which the outer edge of the flow channel is drawn in an image photographed by illuminating the entire flow channel with the optical filter 125 removed from the configuration shown in FIG. 1. FIG. 6(b) shows emission distributions. The images of FIGS. 6(a) and 6(b) are displayed with the same scales, and the position in the drawing is common in the images. Two sample solutions, i.e., a 0.1 N nitric acid solution containing 100 ppm of lead and a 0.1 N nitric acid solution are used, and light emission images are photographed under the condition of voltage application pulse widths of 0.8 msec and 1.8 msec. An image obtained by averaging light emission images corresponding to 96 pulses is shown in FIG. 6(b). The following analysis is performed using this image. In addition, difference images are formed by subtracting the image corresponding to the 0.1 N nitric acid solution from the image corresponding to the 0.1 N nitric acid solution containing 100 ppm of lead under the condition of voltage application pulse widths of 0.8 msec and 1.8 msec, and are displayed together.

In all of the images showing the emission distributions shown in FIG. 6(b), it is found that the light emission is observed in a region protruding greatly from the narrow part of the flow channel shown in FIG. 6(a). Typically, it is found that the light emission can be observed up to a position separated by about 3 mm from the center of the narrow part and the light is emitted in a region much larger than the narrow part. When the length (0.4 mm) of the narrow part is set as a representative size of the narrow part, it is found that the light emission can be observed up to a distance about 8 times the size of the narrow part from the center of the narrow part. This light emission may be thought to be the same as the size of plasma since the light emission is caused by plasma.

In the case of the voltage application pulse width of 0.8 msec, the emission distribution centered around the narrow part of the flow channel is found in both of the solutions. The 0.1 N nitric acid solution contains no lead, and no emission line having such a wavelength as to pass through the optical filter is found from the optical spectrum separately acquired. Whereby, it is thought that the light emission from the 0.1 N nitric acid solution is not atomic emission, but another background light. The reason for the emission intensity from the 0.1 N nitric acid solution containing 100 ppm of lead is greater than the emission intensity from the 0.1 N nitric acid solution is that an emission intensity of atomic emission from the lead is added to a background light intensity.

In the case of the voltage application pulse width of 1.8 msec, the emission distribution centered around the narrow part of the flow channel is found in the 0.1 N nitric acid solution as in the case of 0.8 msec. However, in the case of the 0.1 N nitric acid solution containing 100 ppm of lead, it is found that other than the light emission centered around the narrow part of the flow channel, a local region having a high emission intensity is positioned at a distance of about 2 mm on the left side, that is, on the positive pole side when viewed from the center of the narrow part.

The local emission region present on the positive pole side can be confirmed well in the difference image corresponding to the voltage application pulse width of 1.8 msec. Substantially, this difference image may be thought as an image showing only net light emission of lead, excluding background light, under the condition of a voltage application pulse width of 1.8 msec. In the difference image corresponding to the voltage application pulse width of 0.8 msec, the local light emission at the positive pole side cannot be confirmed, and thus it can be said that in the second light emission, the maximum point of the light emission of lead is positioned at a distance of about 2 mm on the positive pole side. The fact that this maximum point is essentially on the positive pole side and is not essentially on the downstream side of the transmitted sample solution is appreciated from the fact that the maximum point is observed on the positive pole side even when the sample transmission direction is reversed. On the conditions of this embodiment, this maximum point is present at a distance of 5 times the length of the narrow part from the center of the narrow part.

When considering the photograph results in FIGS. 4F to 4H together, the maximum point of the light emission of the lead is equivalent to the position of the air-liquid interface on the positive pole side at the time of the second light emission. In this manner, it is found that there is a specific maximum point of the light emission at the air-liquid interface on the positive pole side. That is, by making the region of the bubbles and the plasma much larger than the narrow part, it is possible to define a clear maximum point of the light emission at a position other than the narrow part. As a result, the measurement is performed in the region other than the narrow part, and the measurement can thus be performed with high detection sensitivity. In addition, it is found that particularly, the measurement can be performed with high detection sensitivity by being performed in the vicinity of the air-liquid interface on the positive pole side. In addition, by causing a plurality of times of light emission with a single voltage application, the characteristics of the light emission can be changed and high-sensitivity measurement can thus be performed.

Figure 7:
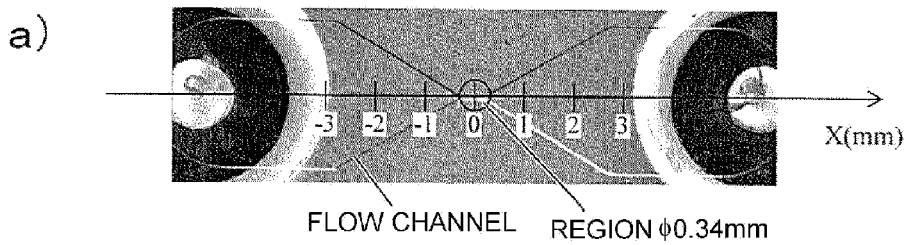
FIG. 7 shows examples of spatial distributions of light emission.
Figure 7:
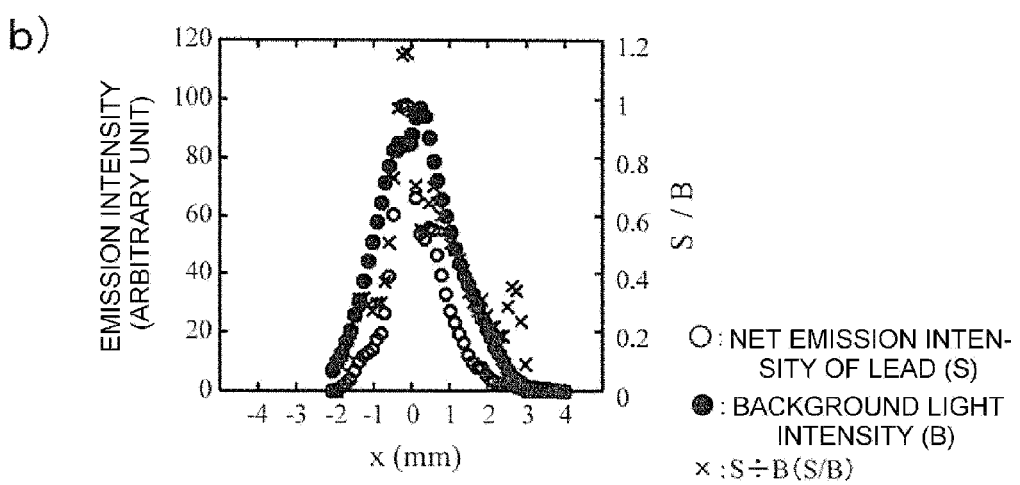
Figure 7:
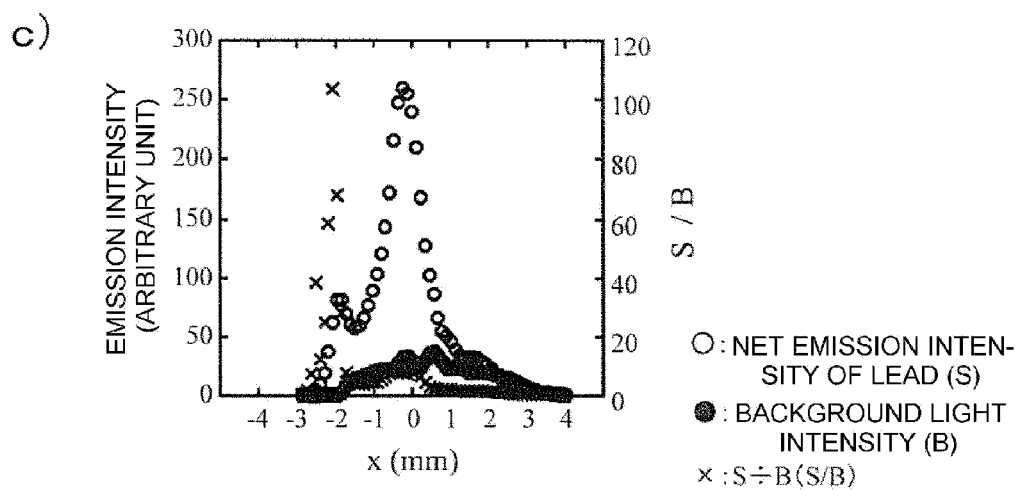

FIG. 7 illustrates the contents of analysis of the emission distributions observed in this embodiment. FIG. 7(a) is a diagram illustrating an analysis object region with respect to an image showing an emission distribution photographed in the manner of FIG. 6. A direction in which two electrodes are connected through the center of the narrow part is set as an x-axis, and the center of the narrow part is defined as x=0. A direction toward the negative pole side, which is on the right side of the drawing, is set as a positive side of the x-axis, and a direction toward the positive pole side, which is on the left side of the drawing, is set as a negative side of the x-axis. On the assumption that the central point of an annular region having a diameter of 0.34 mm is moved on this x-axis, the average emission intensity in that region is calculated.

FIGS. 7(b) and 7(c) are graphs obtained by performing the above-described calculation with respect to an image to be described below. The background light intensity in the drawing is obtained from a background light estimation image in the case of using a band pass filter having a center wavelength of 405 nm and a half-value width of 10 nm as the optical filter 125 of FIG. 1, which is obtained by photographing two light emission images related to a 0.1 N nitric acid solution containing 100 ppm of lead by using, as the optical filter 125 of FIG. 1, two types of band pass filters having a center wavelength of 420 nm and a center wavelength of 450 nm, respectively, with a half-value width of 10 nm, and by performing extrapolation in a wavelength direction in consideration of wavelength dependability of the transmittance of each band pass filter. According to the optical spectrum separately acquired, there is no emission line in the vicinity of wavelengths of 420 nm and 450 nm, and thus it is reasonable that the extrapolation result is estimated as a background light intensity. The net emission intensity of lead in the drawing is obtained from an image obtained by subtracting the above background light estimation image from the image photographed with respect to the 0.1 N nitric acid solution containing 100 ppm of lead by using, as the optical filter 125 of FIG. 1, a band pass filter having a center wavelength of 405 nm and a half-value width of 10 nm.

FIG. 7(b) is an example of the results of analysis of the emission distribution with a voltage application pulse width of 0.8 msec, that is, the emission distribution of the first light emission. A net emission intensity (S) of lead and a background light intensity (B) have an emission distribution around x=0 corresponding to the narrow part. It is found that S/B which is a ratio of S to B exhibits a maximum value in the vicinity of the narrow part.

FIG. 7(c) is an example of the results of analysis of an analysis image, which is obtained by subtracting an analysis image corresponding to a voltage application pulse width of 0.8 msec from an analysis image corresponding to a voltage application pulse width of 1.8 msec, regarding the emission distribution between substantially 0.8 msec and 1.8 msec, that is, the emission distribution of the second light emission. The net light emission of lead exhibits a maximum value in the vicinity of the narrow part, but the distribution is biased to the negative side of the x-axis, that is, the positive pole side, and it is found that a maximum point is present in the vicinity of −2 mm. The background light tends to be high in the vicinity of the narrow part, and be low on both right and left sides, while there is a slight fluctuation.

As compared with the first light emission shown in FIG. 7(b), in the second light emission shown in FIG. 7(c), the emission intensity is high and the background light intensity is low as a whole, and thus S/B is about 10 times greater. Therefore, when the measurement is performed only in the second light emission, detection sensitivity and detection accuracy can be remarkably increased.

It is thought that the reason for the increase of the emission intensity is that such severe experiment conditions are employed that bubbles and plasma are formed larger than the narrow part. It is thought that the reason why the emission intensity of the second light emission is greater than the emission intensity of the first light emission is that such conditions are employed that bubbles are formed sufficiently larger, an element which is an analysis object is scattered in the emission region, and bubbles are formed sufficiently larger, and thus after a current peak is exceeded, the Joule heat production is reduced and the temperature is thus reduced, whereby the movement of the air-liquid interface in which the bubbles are contracted is slow regardless of a reduction of the internal pressure of the bubbles and the pressure is reduced. In addition, the phenomenon in which the background light in the case of the second light emission is less than the background light in the case of the first light emission is a condition of the pressure reduction as described above, and one cause thereof is thought to be a reduction of the frequency of electron recoupling.

Particularly, as found in FIG. 7(c), in the vicinity of −2 mm at the time of the second light emission, the emission intensity of the net light emission of lead is about ⅓ of the maximum value in the narrow part, but exhibits a maximum value, and the background light intensity is very low. As a result, S/B significantly increases. It is found that S/B is about 10 times greater than that of the vicinity of the narrow part at the time of the second light emission, and is about 200 times greater than in the case of the first light emission. The vicinity of −2 mm is equivalent to the vicinity of the air-liquid interface on the positive pole side, and by performing the measurement in this region, detection sensitivity and detection accuracy can be greatly increased.

Particularly, as found in FIG. 7(c), the net light emission of lead is biased to the positive pole side when viewed from the narrow part, and when the region on the positive pole side is set as a center of the measurement object, the net emission intensity increases and a high S/B can also be measured, whereby it is found that detection sensitivity and detection accuracy are greatly increased.

It is thought that one cause is that the efficiency of movement of an element which is an analysis object from the air-liquid interface on the positive pole side to the plasma is increased. It is thought that it is also important for the air-liquid interface to have a convex shape. Also, in the second light emission, the background light intensity is distributed centered around the narrow part, and thus in the measurement on the positive pole side, particularly, in the measurement in the vicinity of the air-liquid interface on the positive pole side, the ratio of the net emission intensity to the background light intensity is high. That is, the measurement can be performed with high detection sensitivity and high detection accuracy. In order to perform the measurement while avoiding the influence of the narrow part having a high background light intensity, because of sufficiently large bubbles and plasma, it is necessary to be able to conduct the measurement of a region excluding the narrow part in the measurement. By performing the measurement out of the narrow part, the background light intensity is reduced, and thus it is possible to realize the measurement with high detection sensitivity and high detection accuracy.

Particularly, as found in FIG. 7(c), it is found that when the center of the measurement object is deviated from the center of the narrow part by about 0.6 mm, 0.8 mm, 1 mm, or 2 mm, the high background light intensity in the narrow part is avoided, the net light emission is sufficiently high, and as a result, a high S/B is obtained. When the length (0.4 mm) of the narrow part is set as a representative size of the narrow part, detection sensitivity and detection accuracy can be greatly increased by setting the distance from the center of the narrow part to the center of the measurement object region to be about 2, 3, or 5 times the size of the narrow part.

In this embodiment, an example of the plasma emission spectrometer has been described. Also, the luminescence phenomenon occurring by electric discharge of a sample solution, and the novel knowledge leading to the invention have been described.

As exemplified and described in this embodiment, in the light emission analysis using electric discharge of the sample solution, it is possible to form bubbles and plasma much larger than the narrow part. In this embodiment, "much larger" corresponds to about 5, 10, or 20 times, but is not limited thereto. A size about 2 to 100 times or greater is also possible and effective.

As exemplified and described in this embodiment, in the light emission analysis using electric discharge of the sample solution, detection sensitivity and detection accuracy can be greatly increased by setting a region other than the narrow part in the flow channel as a measurement object region. Since the light emission is caused due to plasma which is generated in bubbles, it is essential that the bubbles and the plasma spread up to the region other than the narrow part in order to set the region other than the narrow part as a measurement object, and this is possible as exemplified and described in this embodiment. In addition, since the bubbles and the plasma are formed in the flow channel, the object region of measurement is limited to the inside of the flow channel.

As exemplified and described in this embodiment, in the light emission analysis using electric discharge of the sample solution, when a region other than the narrow part in the flow channel is set as a measurement object region, the center of the measurement object region is separated from the center of the narrow part by, for example, about 0.6 mm, 0.8 mm, 1 mm, or 2 mm, and thus detection sensitivity and detection accuracy can be greatly increased. When the length of the narrow part is set as a representative size of the narrow part, the center of the measurement object region is separated from the center of the narrow part by a distance about 2, 3, or 5 times the size of the narrow part, and thus detection sensitivity and detection accuracy can be greatly increased. This distance can also be about 5 times or greater the size, and is effective.

As exemplified and described in this embodiment, net light emission can be biased to the positive pole side by forming bubbles and plasma much larger than the narrow part. In the light emission analysis using electric discharge of the sample solution, detection sensitivity and detection accuracy can be greatly increased by setting a region on the positive pole side as a measurement object region. In this case, it is effective that the region is on the positive pole side of the center of the narrow part of the flow channel. Particularly, when the measurement object region includes a region in the vicinity of the air-liquid interface on the positive pole side, detection sensitivity and detection accuracy can be greatly increased.

As exemplified and described in this embodiment, in the light emission analysis using electric discharge of the sample solution, a plurality of times of light emission can be realized with high reproducibility with a single voltage application. In addition, according to this embodiment, in the light emission analysis using electric discharge of the sample solution, a plurality of times of light emission are caused with a single voltage application and only specific-n-th light emission is measured, and thus it is possible to realize the measurement with high detection sensitivity, high detection accuracy, and high reproducibility. By causing a plurality of times of light emission with a single voltage application, the emission intensity is increased, and particularly, in the second light emission, the measurement can be performed with a high emission intensity. In addition, particularly, in the second light emission, the ratio of the net emission intensity to the background light intensity is high, and thus the measurement can be performed with high detection sensitivity. In this embodiment, the plurality of times is at least 2 times, but is not limited thereto. 2 to 10 or 100 times of light emission can be caused, and is effective.

Embodiment 2

In this embodiment, an example of a plasma emission spectrometer which controls a measurement position and a measurement timing will be described.

Figure 8:
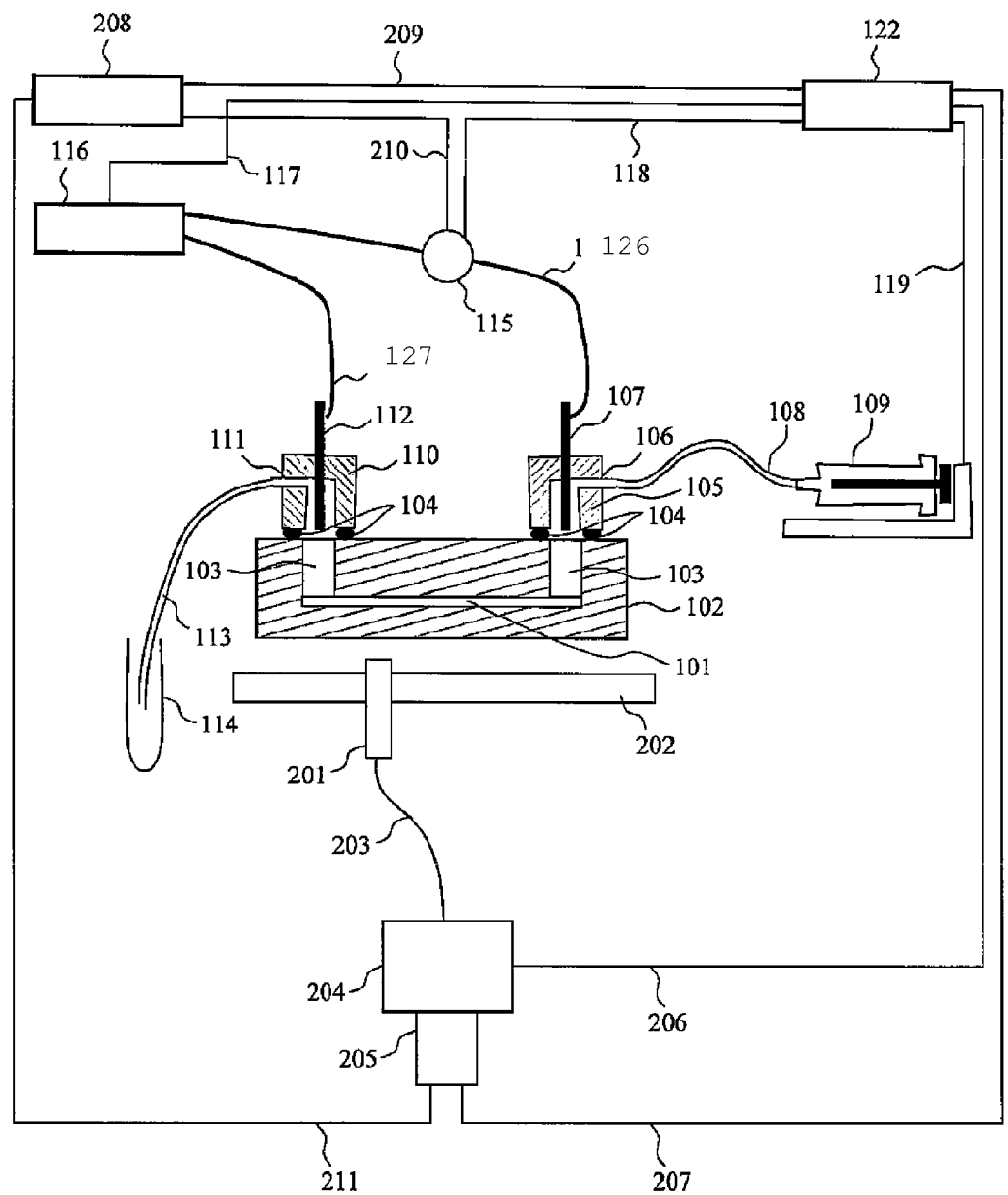
FIG. 8 is a diagram showing an example of a configuration of a plasma emission spectrometer.

FIG. 8 is a diagram showing an example of a configuration of a plasma spectrometer of this embodiment. The parts around a flow channel 101 are the same as in FIG. 1, and detailed descriptions thereof will be omitted.

An optical fiber end 201 is directed to a flow channel 101 and is installed on the opposite side of connectors 105 and 110. The optical fiber end 201 is fixed to a stage 202. Whereby, by moving the stage 202, the optical fiber end 201 can be moved, the position thereof relative to the flow channel 101 can be arbitrarily changed, and the optical fiber end 201 can receive light of light emission from an arbitrary position in the flow channel 101 in distinction from light emission from another position. In the example shown in FIG. 8, the optical fiber end 201 is positioned closer to the positive pole side than the narrow part of the flow channel, and the positive pole side in the flow channel is a measurement object.

The optical fiber end 201 is an end part of an optical fiber 203, and the other end of the optical fiber 203 is connected to a spectroscope 204. The light received by the optical fiber end 201 is input to the spectroscope 204 through the optical fiber 203 and is dispersed. The spectroscope 204 is connected to a computer 122 via a signal wire 206, and can be controlled by the computer 122.

As a detector, a CCD camera 205 having an image intensifier (hereinafter, called II) attached thereto is connected to the spectroscope 204, and receives the light dispersed by the spectroscope 204. The II-attached CCD camera 205 is connected to the computer 122 via a signal wire 207, and can be controlled by the computer 122. Information of the optical spectrum measured by the II-attached CCD camera 205 is recorded in a storing device of the computer 122, and can be processed.

A pulse generator 208 is connected to the computer 122 via a signal wire 209. A signal for controlling a power supply which is output from the computer 122 to a power supply 116 is also input to the pulse generator 208 similarly. The pulse generator 208 is connected to the II-attached CCD camera 205 via a signal wire 211. The pulse generator 208 which receives a signal for controlling the power supply does not completely process the signal, or processes the signal to output the signal as a signal for exposure control for the II-attached CCD camera 205. The II-attached CCD camera 205 receives the signal for exposure control and is operated, and can receive the light dispersed by the spectroscope 204 and obtain an optical spectrum.

In addition, the pulse generator 208 is connected to an ammeter 115 via a signal wire 210. The pulse generator 208 receives information of the current measured by the ammeter 115, and processes and outputs a signal for exposure control for the II-attached CCD camera 205 under pre-set conditions to be able to control the exposure of the II-attached CCD camera 205.

Using the plasma spectrometer shown in FIG. 8, a 0.1 N nitric acid solution containing 100 ppm of lead as a sample solution is supplied to the flow channel 101 and a voltage is applied to measure light emission. The procedures are the same as in Embodiment 1, and detailed descriptions thereof will be omitted. The conditions are as follows. The voltage is 2.5 kV, the voltage application pulse width is 1.8 msec, and the number of pulses is 60.

In this embodiment, with respect to a voltage application pulse width of 1.8 msec, two types of measurements, that is, measurement at a timing corresponding to first light emission from immediately after voltage application being started to 0.8 msec after start of voltage application, and measurement at a timing corresponding to second light emission from a voltage application time of 0.8 msec to a voltage application time of 1.8 msec are conducted. For the first light emission in the former case, the pulse generator 208 of FIG. 8 inputs, to the II-attached CCD camera 205, a signal for causing exposure corresponding to a time period from immediately after voltage application to 0.8 msec after voltage application. In addition, for the second light emission in the later case, the pulse generator 208 inputs, to the II-attached CCD camera 205, a signal for causing exposure corresponding to a time period of 1.0 msec from after 0.8 msec to after 1.8 msec after voltage application.

Figure 9:
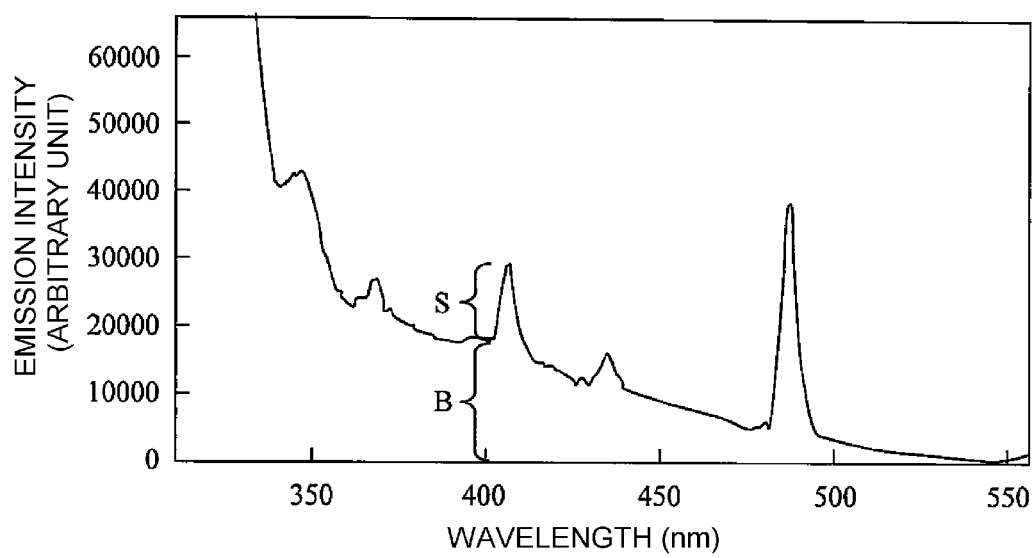
FIG. 9 is a diagram showing an example of an optical spectrum of light emission.

FIG. 9 is a diagram illustrating an example of the optical spectrum of the light emission measured in this embodiment. An emission line (405.78 nm) derived from lead can be confirmed. A net emission intensity of lead is represented by S, and a background light intensity is represented by B.

Figure 10:
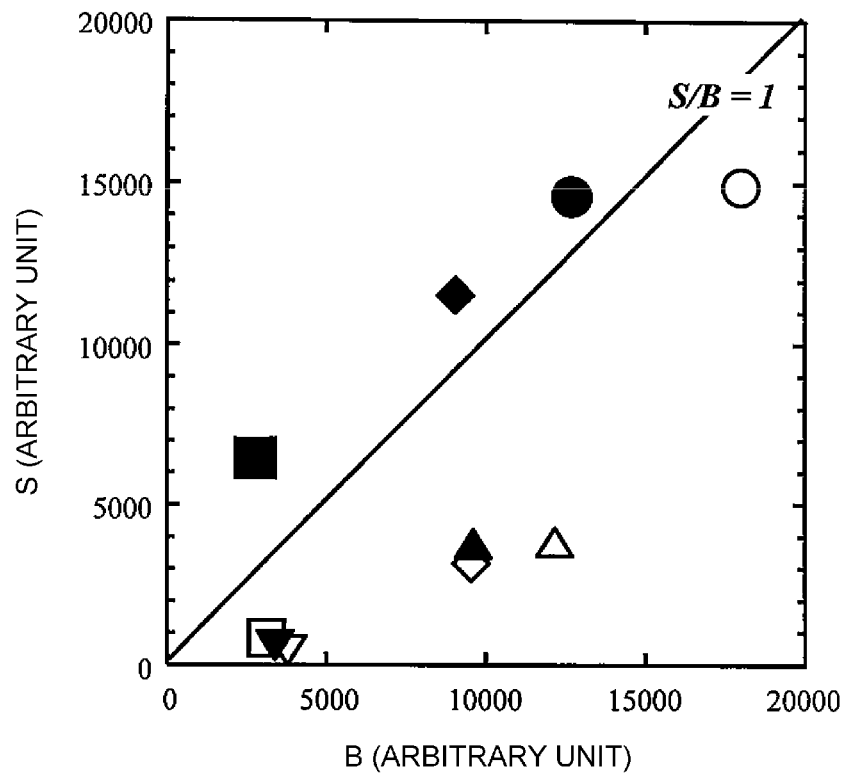
FIG. 10 illustrates results of analysis of measured light emission.

FIG. 10 illustrates the results of analysis of the light emission measured in this embodiment. With regard to the first light emission and the second light emission, an optical spectrum corresponding to 60 pulses is acquired, a set of S and B exemplified in FIG. 9 is calculated, and an average value thereof is displayed. As shown in FIG. 8, the light emission from various positions in the flow channel 101 is examined by moving the optical fiber end 201.

Here, an optical fiber bundle in which 27 fibers having an outer diameter of 230 µm are bundled together is used as the optical fiber 230, and the equivalent diameter of a light reception part of the optical fiber end 201 is about 1.6 mm. Results of the measurement at total 5 positions, that is, the measurement at x=0 corresponding to the narrow part, the measurement at positions at which the center of the optical fiber end 201 which is a center of the measurement object region is separated by 1.15 mm on both right and left sides, and the measurement at positions at which the center of the optical fiber end 201 which is a center of the measurement object region is separated by 2.3 mm on both right and left sides, corresponding to the vicinity of the air-liquid interface in the second light emission, are shown. Coordinate axes are set in the same manner as in FIG. 7(a). Since the radius of the optical fiber end 201 is 0.8 mm, no light emission from the narrow part is measured at 4 positions excluding x=0, and the narrow part is not included as the measurement object region. When a length (0.4 mm) of the narrow part is set as a size of the narrow part, the distance from the center of the narrow part to the measurement object region is about 3 to 6 times the size of the narrow part.

In the measurement for 0.8 msec immediately after voltage application, corresponding to the first light emission, it is found that the net emission intensity (S) is the highest, and the background light intensity (B) is also the highest in the measurement results at x=0 corresponding to the narrow part. In addition, S/B which is a ratio of the net emission intensity to the background light intensity can be expressed by an inclination of a straight line passing through the origin of FIG. 10, and it is found that S/B is smaller than 1 when being below the straight line which is shown in FIG. 10 and expresses S/B=1. In the first light emission, the net emission intensity at another position is less than the measurement result at x=0.

In the measurement from after 0.8 msec to after 1.8 msec after voltage application, corresponding to the second light emission, it is also found that the net emission intensity (S) is the highest, and the background light intensity (B) is also the highest in the measurement results at x=0 corresponding to the narrow part. As compared with the results in the narrow part related to the first light emission, S is almost the same and B is low, and thus S/B increases. Accordingly, it is found that the measurement can be performed with higher detection sensitivity and higher detection accuracy in the second light emission.

In addition, in the second light emission, it is found that in addition to the light emission in the narrow part, S is sufficiently large at a position on the left side of the flow channel in which x on the negative side is −1.15 mm or −2.3 mm, corresponding to the positive pole side. On the positive pole side, S is large and B is small, and thus S/B increases. Thus, it is possible to realize the measurement with high detection sensitivity and high detection accuracy. When the length of the narrow part is set as a representative size of the narrow part, it is shown that the measurement may be conducted at a position separated by a distance about 3 times or greater the size of the narrow part from the narrow part. Particularly, near the air-liquid interface on the positive pole side, S is also sufficiently large and B is very small, and thus S/B is very high and it is possible to realize the measurement with higher detection sensitivity and higher detection accuracy.

In the description of this embodiment, the measurement is performed at a pre-set measurement timing. However, according to the device configuration shown in FIG. 8, the measurement can also be performed only when a current value satisfies a certain condition, so that while the current is measured, the measurement is started when a current value satisfies the condition, and the measurement is terminated when a current value satisfies another condition. For example, it is possible to perform control so that when a current value exceeds a set threshold, the measurement is started simultaneously, and then when a current value is below another set threshold, the measurement is stopped simultaneously. In addition, the measurement can also be performed only in a time zone in which a current value is equal to or higher than a set threshold. For example, although will be described later, in the case of FIG. 13, the measurement is effectively performed with 30 mA as a threshold.

Figure 11:
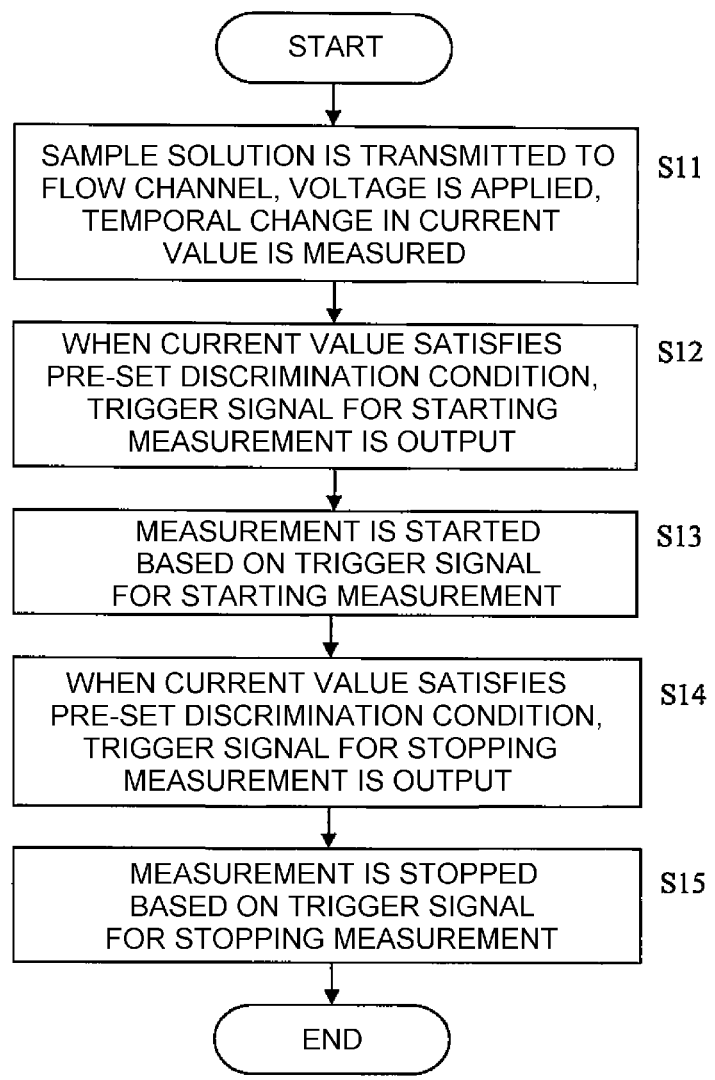
FIG. 11 is a flowchart showing an example of procedures for measuring light emission.

For example, the measurement procedures with respect to the above-described initial example are as shown in the flowchart shown in FIG. 11. That is, a sample solution is transmitted to the flow channel, a voltage is applied, and a temporal change in the current is measured (S11). When a current value satisfies a pre-set discrimination condition, a trigger signal for starting the measurement is output (S12), and the measurement is started based on the trigger signal for starting the measurement (S13). When a current value satisfies a pre-set discrimination condition, a trigger signal for stopping the measurement is output (S14), and the measurement is stopped based on the trigger signal for stopping the measurement (S15). In other cases, the same measurement procedures can be shown.

In this embodiment, the first light emission time and the second light emission time are set as an exposure time. However, better measurement conditions can also be set so that a more restricted exposure time is set.

According to this embodiment, in the light emission analysis using electric discharge of the sample solution, it is possible to realize the measurement with high detection sensitivity, high detection accuracy, and high reproducibility by controlling the measurement timing by using information of the temporal change in the current at the time of voltage application. The above-described "using information of the temporal change in the current at the time of voltage application" includes both of a case in which by using information of temporal change in the current value which has been acquired in advance, the measurement is controlled so as to be conducted in a predetermined time zone, and a case in which while a voltage is applied to the sample solution, a current value thereof is simultaneously monitored and the measurement is controlled in the same voltage application pulse time by using determination standards based on the current value.

A unique effect of this embodiment compared to Embodiment 1 is that the measurement start time and the measurement termination time are freely set, and the measurement is performed according to two time zones, and thus a process called difference is not required. In addition, another unique effect is that the light emission measurement can be controlled by directly using the measured current value. In addition, a further unique effect is that a specific position is selected in the flow channel and the measurement can be performed at a specific timing.

In this embodiment, the measurement position can be moved. However, a device configuration can also be employed in which the measurement position is fixed to a pre-set position. In addition, in this embodiment, only one optical fiber bundle is used, and light emission only from one position is measured at a time. However, a plurality of positions can be set, and light emission from the plurality of positions can be measured simultaneously. In addition, in this embodiment, the measurement is performed at the measurement position which is determined not on the flow channel side, but on the measuring device side. However, the measurement position can also be determined through a window, which is formed using a light-impermeable material at a specific position in the flow channel, to perform the measurement.

In this embodiment, the measurement timing is controlled by using the II-attached CCD camera. However, a device configuration can also be employed in which in place of the II-attached CCD camera, a shutter is used to control the measurement timing. In that case, the device may be configured so that a control signal is transmitted to the shutter.

Embodiment 3

In this embodiment, an example of a plasma emission spectrometer which controls a time domain to perform measurement and analysis by using information of a measured current value will be described.

Figure 12:
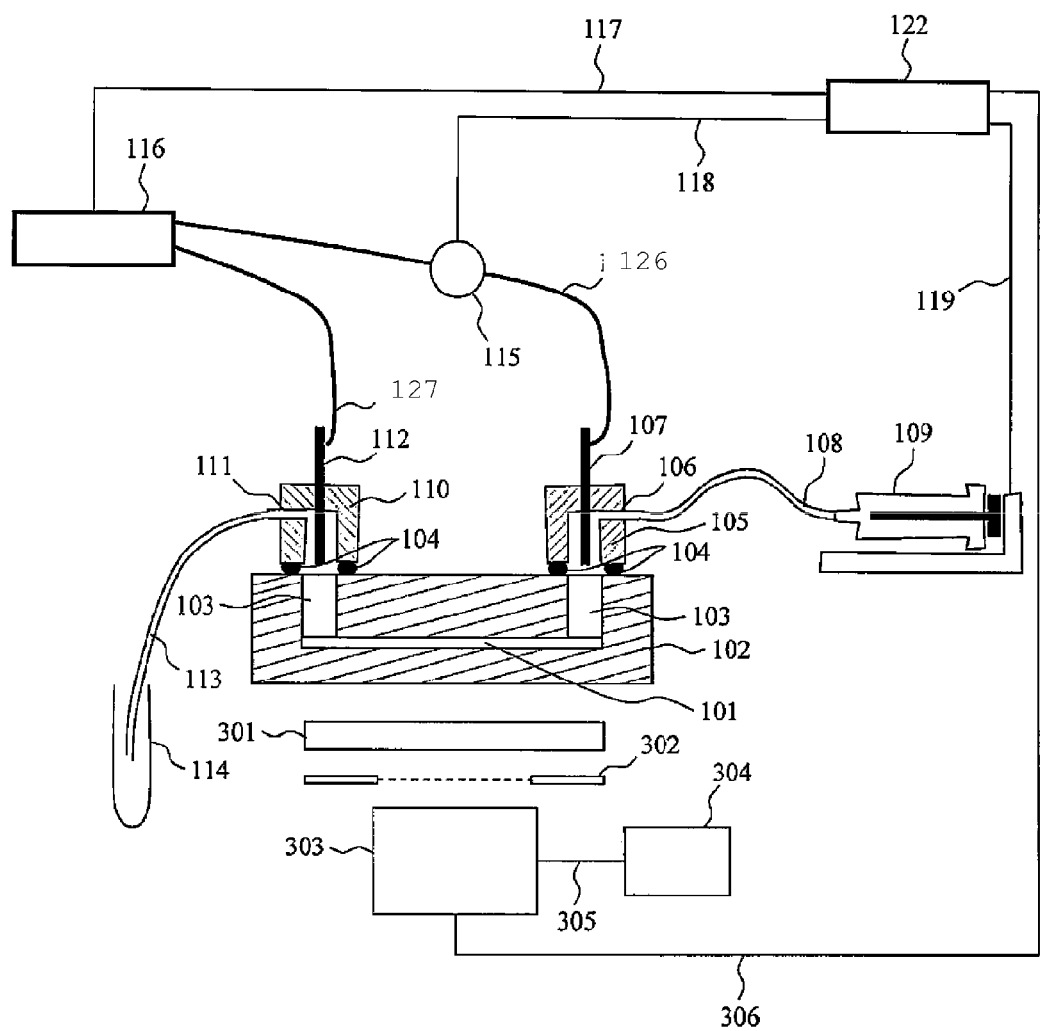
FIG. 12 is a diagram showing an example of a configuration of a plasma emission spectrometer.

FIG. 12 is a diagram showing an example of a configuration of a plasma spectrometer of this embodiment. The parts around a flow channel 101 are the same as in FIG. 1, and detailed descriptions thereof will be omitted.

An optical filter 301 is installed adjacent to the flow channel 101 and is installed on the opposite side of connectors 105 and 110. An optical slit 302 is installed on the back of the optical filter 301, and a photomultiplier 303 is installed immediately behind the optical slit 302. A high-voltage power supply 304 for a photomultiplier is connected to the photomultiplier 303 via an electric wire 305 to supply electric power to the photomultiplier 303. The output from the photomultiplier 303 is recorded and analyzed in a memory of a computer 122 via a signal wire 306.

Using the plasma emission spectrometer shown in FIG. 12, a 0.1 N nitric acid solution containing 100 ppm of lead as a sample solution is supplied to the flow channel 101 and a voltage is applied to measure light emission. The procedures are the same as in Embodiment 1, and detailed descriptions thereof will be omitted. The conditions are as follows. The voltage is 2.5 kV, the voltage application pulse width is 1.8 msec, and the number of pulses is 100.

Figure 13:
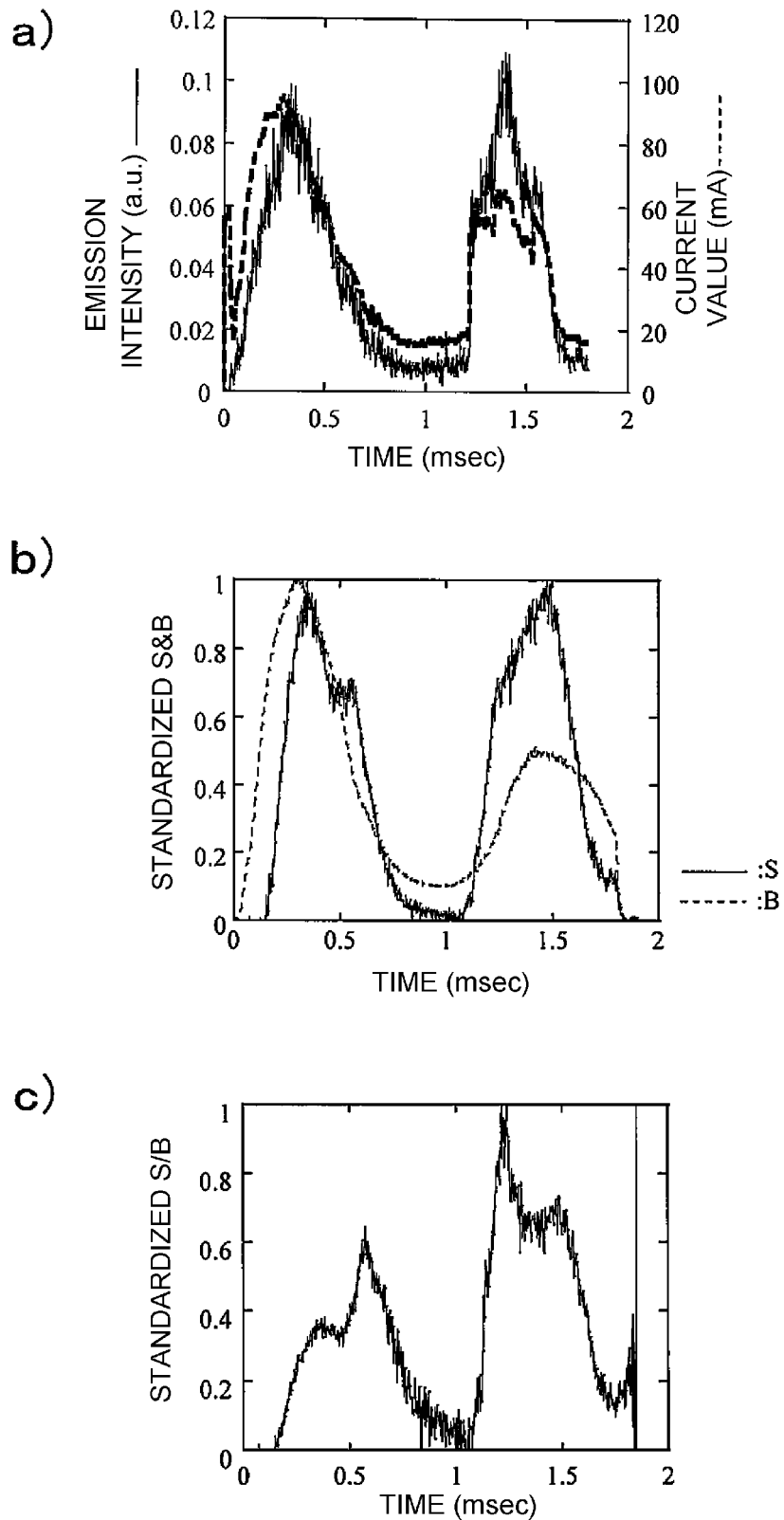
FIG. 13 shows temporal changes in light emission and a current, temporal changes in net light emission and background light, and temporal changes in a ratio of net light emission to background light.

FIG. 13 illustrates an example of the results of the analysis of the light emission measured in this embodiment.

FIG. 13($a$) is a graph in which a temporal change in the light emission and a temporal change in the current are simultaneously recorded by using a band pass filter having a center wavelength of 405 nm and a half-value width of 10 nm as the optical filter 301. The broken line represents a current waveform measured by an ammeter 115, and the solid line represents emission intensity measured by the photomultiplier 303. In the first light emission, it is found that the peak of the light emission is slightly later than the peak of the current in terms of time. In addition in the second light emission, it is found that the emission intensity rapidly increases in response to a rapid increase of the current, and the emission intensity rapidly decreases in response to a reduction of the current.

FIG. 13($b$) is a graph showing temporal changes of net light emission (S) of lead and background light (B). The solid line represents the net light emission (S) of lead, and the broken line represent the background light (B). Data corresponding to 100 pulses which is averaged and standardized by maximum values thereof is shown. From these results, it is found that the behaviors of the temporal changes of S and B are not the same as each other. For example, in the first light emission, it is found that S is emitted later than B, but in the second light emission, S rises earlier than B.

FIG. 13($c$) is a graph showing a temporal change in the ratio (S/B) of the net light emission (S) of lead to the background light (B). A temporal change in the S/B which is calculated based on the temporal changes of S and B calculated by averaging data corresponding to 100 pulses and is standardized by a maximum value is shown. It is found that S/B in the second light emission is generally higher than that in the first light emission. That is, when the second light emission is measured, S/B is high, and as a result, it is possible to realize the measurement with high detection sensitivity. In addition, it is found that during the first light emission, S/B is high in a second half. A cause thereof is that S rises later than B. When a second half of the first light emission is measured, S/B is high, and thus it is possible to realize the measurement with high detection sensitivity. In addition, in the second light emission, it is found that S/B is high in a part immediately after the light emission. A cause thereof is that S rises more rapidly than B. Accordingly, when a first half of the second light emission is measured, S/B is high, and thus it is possible to realize the measurement with high detection sensitivity.

In the above measurement, a setting can be provided in which the measurement is performed from a pre-set measurement start time to a measurement termination time after voltage application, or is performed for the whole time period over the whole area of the voltage application pulse width to record data in a storing device such as a memory of the computer and to select and use measurement results in a predetermined time zone upon analysis.

The method described herein can also be conducted by performing a pre-scan. For example, before the final measurement, a temporal change in the plasma emission is measured through a pre-scan, and results of the pre-scan are subjected to arithmetic processing to estimate a time slot in which the emission intensity from a measurement object substance is high. As can be guessed from FIG. 13(b), for example, it is sufficiently effective to select a region in which a ratio of the emission intensity from the measurement object substance to a maximum value of the emission intensity is 0.3 or greater. Thereafter, when the measurement is conducted in this time slot, it is possible to perform the measurement with high sensitivity.

Similarly, for example, before the final measurement, a temporal change in the plasma emission is measured through a pre-scan, and results of the pre-scan are subjected to arithmetic processing to estimate a time slot in which a ratio of the net emission intensity from the measurement object substance to the background light intensity from substances other than the measurement object substance is high. As can be guessed from FIG. 13(c), for example, it is sufficiently effective to select a region in which a ratio of the ratio of the net emission intensity from the measurement object substance to the background light intensity from substances other than the measurement object substance to a maximum value of the ratio of the net emission intensity from the measurement object substance to the background light intensity from substances other than the measurement object substance is 0.3 or greater. Thereafter, when the measurement is conducted in this time slot, it is possible to perform the measurement with high sensitivity.

Similarly, for example, before the final measurement, a temporal change in the plasma emission is measured through a pre-scan, and results of the pre-scan are subjected to arithmetic processing to estimate a time slot in which a variation in emission intensity from the measurement object substance is small. For example, it is sufficiently effective to select a region in which a coefficient of variation is 10% or less. For example, when the number of times of voltage application is set to 100 and the measurement results are integrated, a coefficient of variation is proportional to 1/the 0.5-th power of the number of times of integration, and thus it is possible to conduct the measurement with high accuracy in which the coefficient of variation is finally 1% or less.

A unique effect of this embodiment compared to Embodiment 2 is that it is not necessarily required to pre-set a measurement time. Data of the temporal changes in the current and the light emission corresponding to the whole time period in the voltage application time can be recorded in the storing device, and after acquisition of the data, the data can be processed to set an appropriate measurement time zone and analysis can be performed. Accordingly, S/B is high, and thus it is possible to securely obtain measurement results with high detection sensitivity.

Embodiment 4

In this embodiment, an example of a plasma emission spectrometer which measures a temporal change in the current simultaneously when applying an electric field to a sample solution and measuring light emission, adjusts a composition of a reference solution to match the temporal change, measures light emission of the reference solution after adjustment, and estimates the amount of an analysis object substance in the sample solution by using the measured emission intensity will be described.

Using the plasma emission spectrometer shown in FIG. 12, a 0.1 N nitric acid solution containing 100 ppm of lead as a sample solution is supplied to a flow channel 101 and a voltage is applied to measure light emission. The procedures are the same as in Embodiment 1, and detailed descriptions thereof will be omitted. The conditions are as follows. The voltage is 2.5 kV, the voltage application pulse width is 0.8 msec, and the number of pulses is 100.

Figure 14:
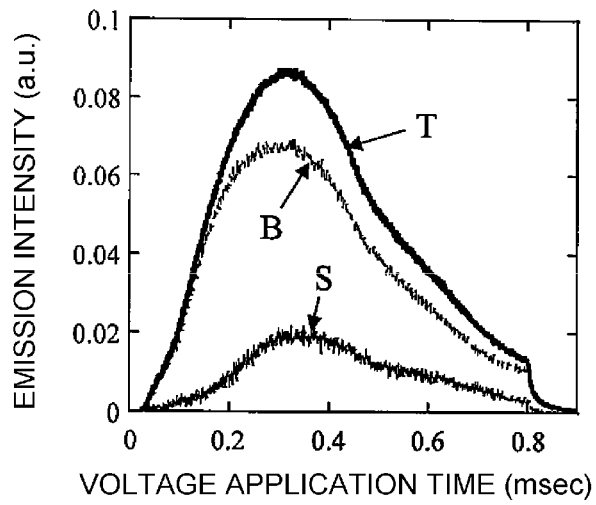
FIG. 14 shows an example of analysis using a reference solution.
Figure 14:
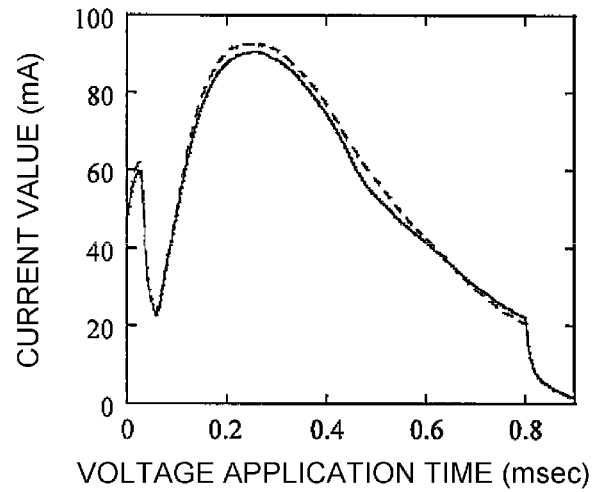
Figure 14:
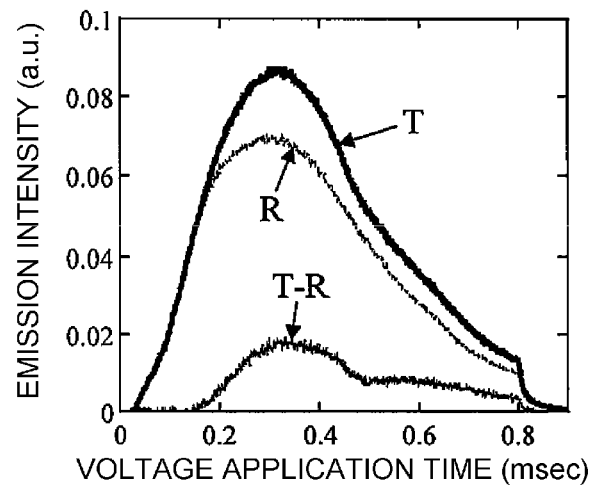

FIG. 14 shows an example of analysis in which a reference solution is adjusted and light emission thereof is measured and used in estimation of a net emission intensity from an analysis object substance in a sample solution.

FIG. 14(a) is a graph showing a temporal change (represented by T in FIG. 14(a)) in the light emission which is measured by using a band pass filter having a center wavelength of 405 nm and a half-value width of 10 nm as an optical filter 301, and temporal changes in the net light emission (S) of lead and background light (B). The background light (B) is extrapolated and estimated in the same manner as in the method described in Embodiment 1 from the results of the measurement using band pass filters having a center wavelength of 420 nm and a center wavelength of 450 nm, respectively, with a half-value width of 10 nm. In other words, background intensity is estimated using information of the results of the measurement at other wavelengths. The net emission intensity (S) of lead is calculated by subtracting the background light (B) guessed using the information of the results of the measurement at other wavelengths from the emission intensity (T) measured by the band pass filter having a center wavelength of 405 nm and a half-value width of 10 nm.

FIG. 14(b) shows a temporal change in the current which is acquired in the measurement of FIG. 14(a), and a temporal change in the current when the measurement is performed using a reference solution which is adjusted by changing proportions of a concentrated nitric acid and water to match the temporal change. The solid line represents the temporal change in the current in the sample solution, and the broken line represents the temporal change in the current in the reference solution after adjustment. Each result is an average corresponding to 100 pulses. It is found that the temporal change in the current of the reference solution and the temporal change of the current of the sample solution can be allowed to coincide with each other by adjusting a mixing ratio between the concentrated nitric acid and the water.

FIG. 14(c) shows a temporal change (T) in the light emission measured using a band pass filter having a center wavelength of 405 nm and a half-value width of 10 nm as the optical filter 301, which is the same as shown in FIG. 14(a), a temporal change (R) in the light emission which is measured using the same filter with respect to the reference solution shown in FIG. 14(b), and a temporal change (T-R) in the net emission intensity of lead which is calculated by interpreting and subtracting the above-described light emission of the reference solution as background light. That is, the emission intensity of the reference solution is estimated to be the same as the background light intensity.

It is found that the temporal changes in the net emission intensity of lead obtained in FIGS. 14(a) and 14(c) almost coincide with each other, and the emission intensity of the reference solution prepared using the method of FIG. 14(b) can be used as an estimated value of the background light. That is, the net emission intensity from the analysis object substance in the sample solution can be estimated by using the emission intensity of the prepared reference solution. When accurately knowing the net emission intensity, it is possible to accurately guess the amount of the analysis object substance in the sample solution.

In general, the composition of the sample solution is not known. Accordingly, in order to match temporal changes of the current, it is necessary to record temporal changes in the current of solutions having slightly different mixing ratios each other and to determine the composition of the reference solution so that the temporal changes in the current are matched. Even when a main solution composition is known, a temporal change of the current in the case in which light emission is caused by actually applying a voltage to a solution which has been separately adjusted is different from that of the sample solution. Even when the electrical conductivity of the sample solution is measured and the reference solution is adjusted so as to match the numerical value of the electrical conductivity, there is a difference in the temporal change in the current due to a subtle mismatch. Factors which determine the temporal change in the current not only include the electrical conductivity of the solution, but also depend on a generation status of bubbles and plasma, states of impurities and adhering bubbles in the flow channel, and the like. Therefore, only by matching the electrical conductivities, the temporal changes in the current cannot be allowed to coincide with each other, and thus it cannot be thought that the emission intensity of the reference solution is the same as that of the background light. On the other hand, when using a reference solution adjusted so that the temporal change of the current at the time of voltage application and that of the sample solution are matched, the emission intensity of the reference solution may be thought to be the same as that of the background light of the sample solution as described above.

In general, the reference solution can be adjusted by combining water and an acid such as a nitric acid which is predicted to constitute a main part of the sample solution. It is also appropriate to combine other acids such as a hydrochloric acid and a sulfuric acid which are frequently used in elemental analysis. Since it is important that there is electrical conduction, a solution containing salts such as sodium chloride can also be combined. In addition, when the sample solution contains an organic solvent, it is also appropriate to combine the organic solvent.

Figure 15:
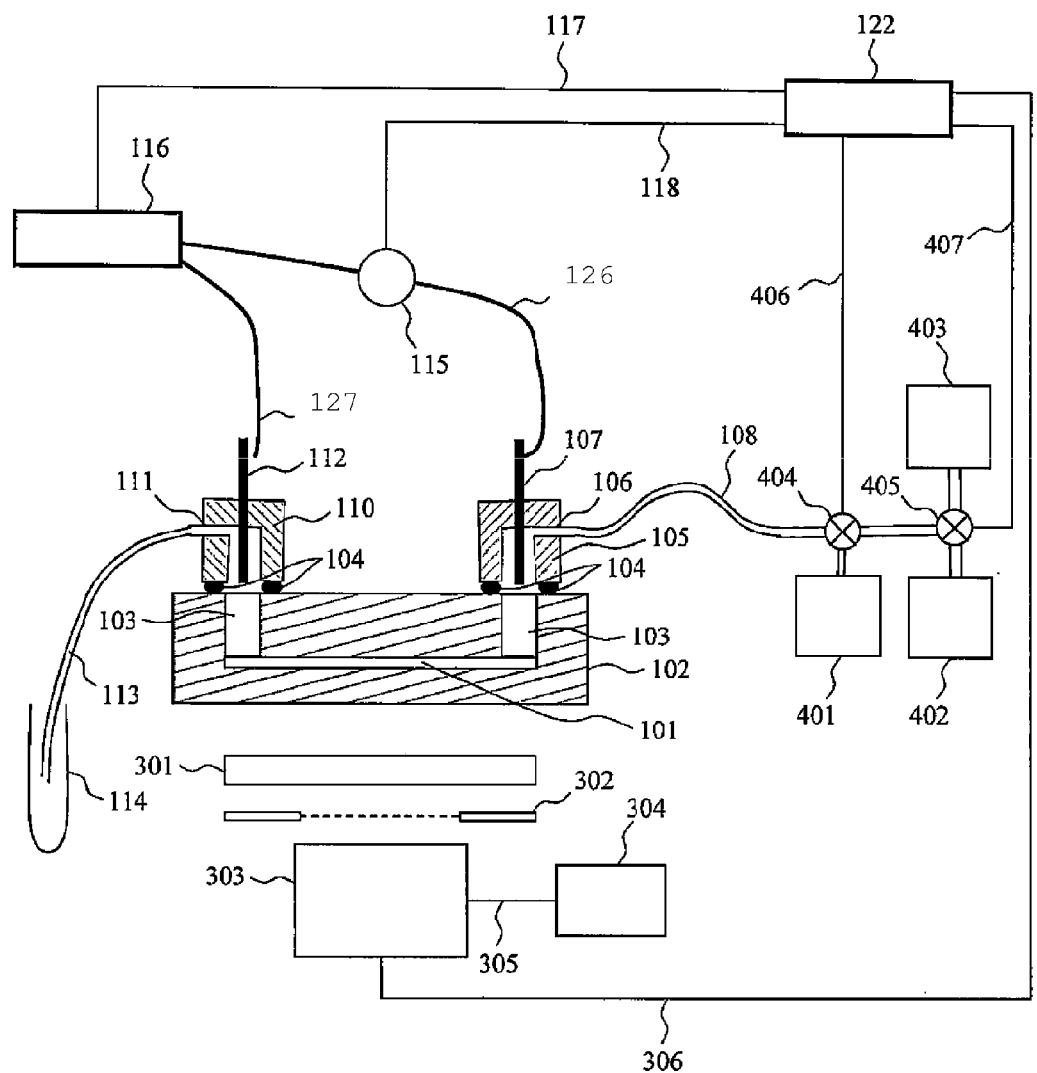
FIG. 15 is a diagram showing an example of a configuration of a plasma emission spectrometer.

FIG. 15 is a diagram showing an example of a configuration of another plasma emission spectrometer of this embodiment. The parts around a flow channel 101 and the measurement-related parts around a photomultiplier 303 are the same as in FIG. 12, and detailed descriptions thereof will be omitted. In addition, although a description related to a syringe pump 109 is omitted, a device for liquid transmission equivalent thereto is provided.

A sample solution container 401 which sets a sample solution is connected to a pipe 108 via a switching valve 404. Containers 402 and 403 into which a solution for adjusting a reference solution is put are connected to the pipe 108 via a mixer 405. The switching valve 404 and the mixer 405 are connected to a computer 122 via signal wires 406 and 407, respectively. The sample solution or the reference solution which may be during the course of adjustment can be transmitted to the flow channel 101 by switching the switching valve 404 with a signal from the computer 122. In addition, the solutions in the containers 402 and 403 can be mixed at an arbitrary ratio and transmitted by operating the mixer 405 with a signal from the computer 122. A combination of a solution for adjusting the reference solution is the same as in the above description.

Figure 16:
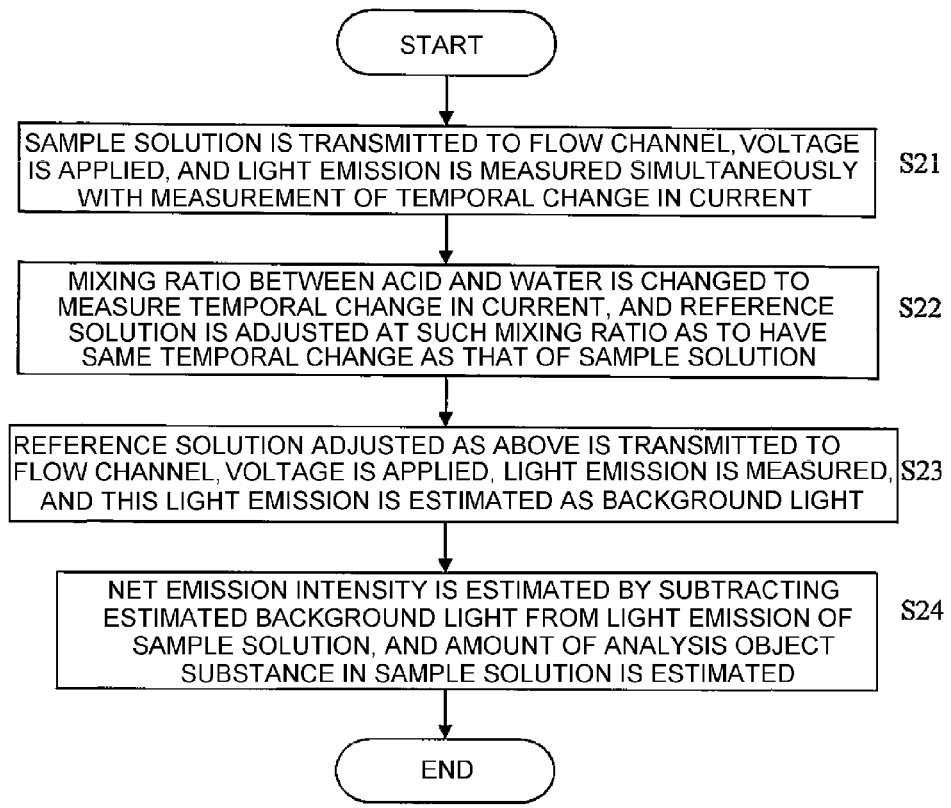
FIG. 16 is a flowchart illustrating analysis procedures.

FIG. 16 is a flowchart showing measurement procedures in this embodiment. First, a sample solution is transmitted to the flow channel, a voltage is applied, and light emission is measured simultaneously with the measurement of a temporal change in the current (S21). Next, a mixing ratio between an acid and water is changed, a temporal change in the current is measured, and the acid and the water are mixed at such a mixing ratio that the temporal change in the current is the same as that of the sample solution, whereby a reference solution is adjusted (S22). Next, the adjusted reference solution is transmitted to the flow channel, a voltage is applied, light emission is measured, and this light emission is estimated as background light (S23). Finally, a net emission intensity is estimated by subtracting the estimated background light from the light emission of the sample solution, and using the estimated net emission intensity, the amount of an analysis object substance in the sample solution is estimated (S24).

By accurately estimating the background light intensity, a net light emission amount derived from the analysis object substance can be accurately estimated, and thus detection sensitivity and detection accuracy with respect to the analysis object substance in the sample solution can be improved. In addition, since it is not necessary to use other wavelength information in the estimation of the background light, the device configuration can be simplified so that, for example, only a single optical filter can be used.

When knowing the type of the acid in the sample solution, it is preferable to use the same type of acid in the reference solution. In many cases, it is appropriate to use a nitric acid since the nitric acid is frequently used in elemental analysis. In many cases, since an acid is used in elemental analysis, there is an assumption that the reference solution is prepared by mixing the acid with water. However, when the electrical conductivity of the sample solution is derived mainly from the salt dissolved, it is also appropriate to mix a solution containing corresponding salt at a high concentration with water to prepare the reference solution.

Regarding the reference solution, it is also effective to perform the adjustment by blending a solution not containing the analysis object substance and a solution containing the analysis object substance. In general, in the estimation of the amount of the analysis object substance in the sample solution, several solutions containing the analysis object substance at a known concentration are prepared to perform the measurement, and a calibration curve using the light emission amounts is plotted and used. However, an analysis object substance-containing solution in which a temporal change in the current is matched may be prepared as a reference solution, and a calibration curve showing a net light emission amount corresponding to the concentration may be plotted and used. By using the reference solution in which a temporal change in the current is matched, a more accurate calibration curve can be plotted, and detection sensitivity, detection accuracy, and reproducibility can be improved.

According to this embodiment, when a temporal change in the current is measured simultaneously when an electric field is applied to a sample solution and light emission is measured, a composition of a reference solution is adjusted to match the temporal change, and light emission of the reference solution after adjustment is measured to estimate a net emission intensity of the sample solution, it is possible to realize a plasma emission spectrometer having high detection sensitivity and high detection accuracy.

In this embodiment, the light emission beyond the optical filter is measured by the photomultiplier, and a temporal change in the light emission is also measured. However, the measurement of the light emission is not limited to this means, and it is not necessarily required to measure the temporal change in the light emission. A spectroscope may be used, and an optical detector such as a CCD camera, a photodiode, and a photodiode array is also properly used. In the current measurement, temporal changes are measured, and it is important to compare the temporal changes in the current and to allow the temporal changes in the current to coincide with each other through solution adjustment.

According to this embodiment, even when using only one sheet of an optical filter, it is possible to accurately estimate a net emission intensity, and thus detection sensitivity and detection accuracy can be improved. In general, in order to estimate a net emission intensity and a background light intensity, it is necessary to disperse the light by using a plurality of optical filters, a diffraction grating, or the like. However, since the measurement can be performed only with one sheet of an optical filter, the device configuration can be simplified, the device can be miniaturized, and as a result, it is possible to realize an inexpensive spectrometer.

Embodiment 5

In this embodiment, an example of another configuration of the plasma emission spectrometer will be described, and novel knowledge leading to the invention will be described.

Figure 17:
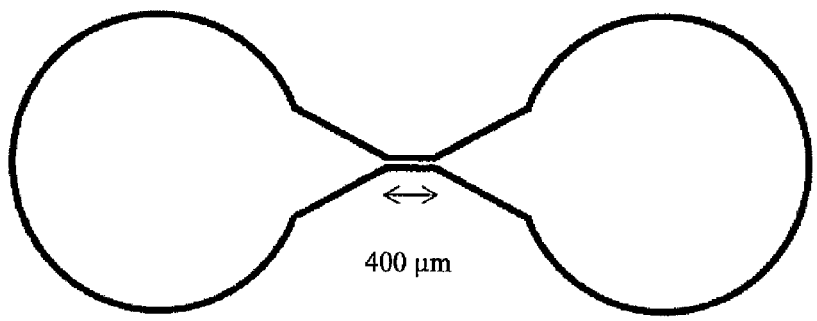
FIG. 17 is a diagram illustrating an example of a flow channel.

FIG. 17 is a diagram illustrating an example of a flow channel used in this embodiment. The flow channel has a narrow part having a length of 400 μm. The depth of the flow channel is 33 μm. Electrodes are installed at right and left ends of the flow channel. The left side of FIG. 17 is set as a negative pole, and the right side of FIG. 17 is set as a positive pole.

The flow channel shown in FIG. 17 is filled with a 0.1 N nitric acid solution having 50 ppm of potassium as a sample solution, and a voltage of 1260 V is applied for 30 msec. In this embodiment, after the sample solution is filled in the flow channel, the voltage is applied without liquid transmission. The observation is performed using a high-speed camera.

Figure 18A:
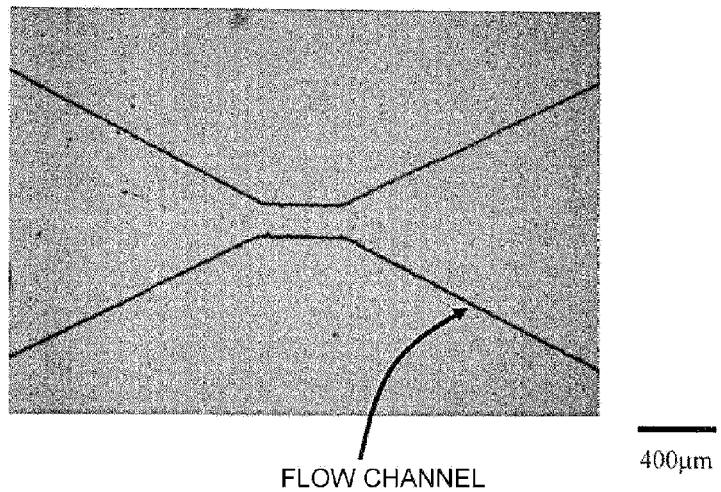
FIG. 18A is an image showing a state before voltage application.

FIG. 18A is an example of an image obtained by photographing a state of the flow channel before voltage application. A region surrounded by the wall of the flow channel shown by the arrow in FIG. 18A is filled with a sample solution, and at this time point, no air-liquid interfaces and light emission are present.

Figure 18B:
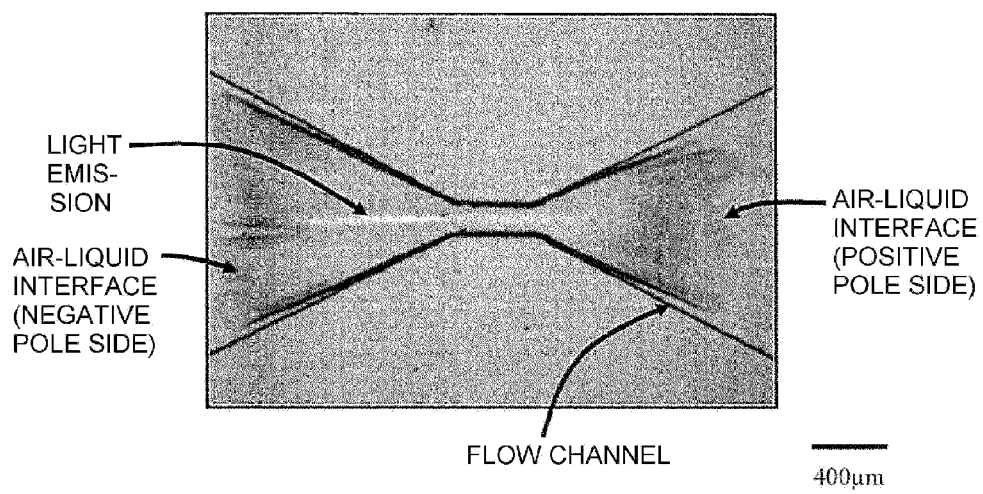
FIG. 18B is an image showing bubbles and a light emission state.

FIG. 18B is an example of an image obtained by photographing a state of the flow channel after 100 microseconds after voltage application. Similarly to FIG. 4A, air-liquid interfaces are shown on both right and left sides when being viewed from the center of the narrow part. The left side corresponds to the air-liquid interface on the negative pole side, and the right side corresponds to the air-liquid interface on the positive pole side. A part interposed between both the air-liquid interfaces of the flow channel including the narrow part corresponds to bubbles, and apart outside the air-liquid interface corresponds to the sample solution when viewed from the narrow part. Light emission linearly extending in a horizontal direction can be observed in the central part of the image of FIG. 18B. This is light emission from a potassium solution. It is found that this light emission is strong on the negative pole side on the left side from the center of the narrow part, and reaches the air-liquid interface on the negative pole side.

Figure 19:
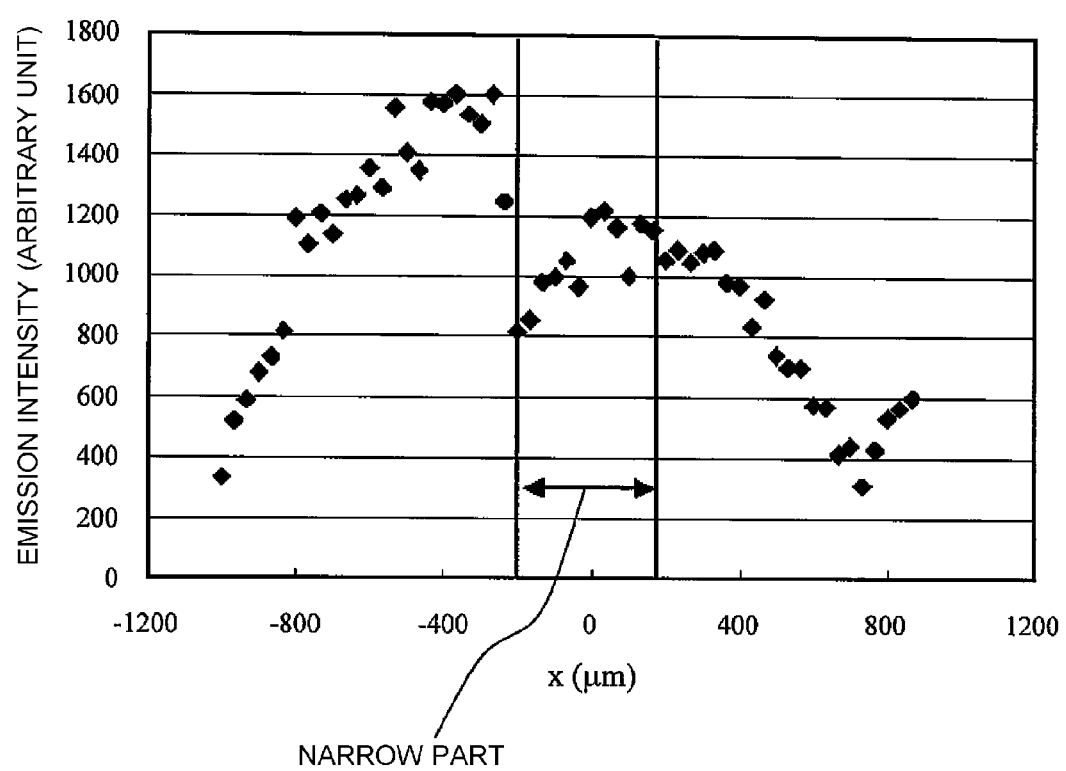
FIG. 19 is a diagram showing an example of a spatial distribution of light emission.

FIG. 19 shows a distribution of the emission intensity from the potassium solution with respect to an x-axis corresponding to the horizontal direction of FIG. 18. The center of the narrow part is set as x=0. In FIG. 19, a region of x corresponding to the narrow part is shown. As found from FIG. 19, it is found that the emission intensity from the potassium solution is high on the negative pole side rather than the narrow part. The emission intensity is highest at a position which is positioned at a distance of about 400 μm when measured from the center of the narrow part, and this distance is about 1 time the length (400 μm) of the narrow part.

As found from FIGS. 18B and 19, when the measurement is performed on the negative pole side when viewed from the center of the narrow part, high-sensitivity measurement can be conducted. Similarly, when the measurement is performed in the vicinity of the air-liquid interface on the negative pole side, high-sensitivity measurement can be conducted.

The invention is not limited to the embodiments, and includes various modification examples. For example, the embodiments are described in detail to describe the invention in an easily understood manner, and are not necessarily limited to the embodiments that include all configurations described above. A part of the configuration of an embodiment can be replaced by the configuration of another embodiment, and the configuration of an embodiment can be added to the configuration of another embodiment. Addition, deletion, and replacement of other configurations are also possible for a part of the configurations of the embodiments.

The functions, the processing parts, the processing means, and the like of the configurations may be realized by hardware by designing, for example, some or all of the components by an integrated circuit. In addition, a processor may interpret and execute programs for realizing the functions to realize the configurations, the functions, and the like by software. Information, such as programs, tables, and files, for realizing the functions can be stored in a recording device, such as a memory, a hard disk, and a solid state drive (SSD), or on a recording medium, such as an IC card, an SD card, and a DVD.

In addition, only the signal wires and the electric wires which are thought to be necessary for the description are shown, and the embodiments are not necessarily limited to the embodiments showing all of control wires and information wires in the product. It may be thought that actually, almost all of the configurations are connected to each other.

In the embodiments, the limited element, solution composition, flow channel shape, and measurement conditions have been used as an example and described, but the invention is not limited to the element, solution composition, flow channel shape, and measurement conditions described in the embodiments.

REFERENCE SIGNS LIST

101: FLOW CHANNEL
102: QUARTZ GLASS
103: THROUGH HOLE
104: O-RING
105, 110: CONNECTOR
106, 111: PIPE CONNECTING PORT
107, 112: ELECTRODE
108, 113: PIPE
109: SYRINGE PUMP
114: WASTE LIQUID CONTAINER
115: AMMETER
116: POWER SUPPLY
117, 118, 119, 120: SIGNAL WIRE
121: CAMERA
122: COMPUTER
123, 124: LENS
125: OPTICAL FILTER
126, 127: high-voltage electric wire
201: OPTICAL FIBER END
202: STAGE 203: OPTICAL FIBER
204: SPECTROSCOPE
205: IMAGE INTENSIFIER-ATTACHED CCD CAMERA
206, 207, 209, 210, 211: SIGNAL WIRE
208: PULSE GENERATOR
301: OPTICAL FILTER
302: OPTICAL SLIT
303: PHOTOMULTIPLIER
304: POWER SUPPLY FOR PHOTOMULTIPLIER
305, 306: SIGNAL WIRE
401: SAMPLE SOLUTION CONTAINER
402, 403: CONTAINER FOR REFERENCE SOLUTION ADJUSTMENT
404: SWITCHING VALVE
405: MIXER
406, 407: SIGNAL WIRE

The invention claimed is:

1. A plasma spectrometer comprising:
a flow channel which has a narrow part in the middle and is supplied with a sample solution;
a pair of electrodes which are disposed with the narrow part interposed therebetween to apply a voltage to the flow channel; and
a measuring part which disperses and measures plasma emission which is caused in bubbles formed in the flow channel due to the voltage application,
wherein the measuring part is focused to receive light from a region other than the narrow part of the flow channel as a measurement object region.

2. The plasma spectrometer according to claim 1, wherein a center of the measurement object region is separated from a center of the narrow part by a distance 1 time or greater a dimension of the narrow part in a flow channel direction.

3. The plasma spectrometer according to claim 1, wherein the measurement object region is a region between the narrow part and a positive electrode of the pair of electrodes.

4. The plasma spectrometer according to claim 1, wherein the measurement object region includes the vicinity of an air-liquid interface on a positive electrode side of the pair of electrodes.

5. The plasma spectrometer according to claim 1, wherein the measurement object region is a region between the narrow part and a negative electrode of the pair of electrodes.

6. The plasma spectrometer according to claim 1, wherein the measurement object region includes the vicinity of an air-liquid interface on a negative electrode side of the pair of electrodes.

7. The plasma spectrometer according to claim 1,
wherein one or more specific times of light emission after second light emission are measured among a plurality of times of plasma emission which are caused with a single voltage application to the flow channel.

8. The plasma spectrometer according to claim 7, wherein the second light emission is measured among the plurality of times of plasma emission.

9. The plasma spectrometer according to claim 8, wherein the second light emission is measured for a first half of an emission time of the second light emission.

* * * * *